(12) United States Patent
Greenberg et al.

(10) Patent No.: US 9,618,441 B2
(45) Date of Patent: Apr. 11, 2017

(54) DETERMINATION OF PORE SIZE IN POROUS MATERIALS BY EVAPORATIVE MASS LOSS

(75) Inventors: Alan R. Greenberg, Boulder, CO (US); William B. Krantz, Boulder, CO (US); Elmira Kujundzic, Erie, CO (US); Adrian Yeo, Singapore (SG); Seyed Saeid Hosseini, Singapore (SG)

(73) Assignees: National University of Singapore, Singapore (SG); The Regents of the University of Colorado, A Body Corporate, Denver, CO (US)

(*) Notice: Subject to any disclaimer, the term of this patent is extended or adjusted under 35 U.S.C. 154(b) by 261 days.

(21) Appl. No.: 13/695,251

(22) PCT Filed: May 2, 2011

(86) PCT No.: PCT/US2011/034853
§ 371 (c)(1),
(2), (4) Date: Oct. 29, 2012

(87) PCT Pub. No.: WO2011/137454
PCT Pub. Date: Nov. 3, 2011

(65) Prior Publication Data
US 2013/0042670 A1    Feb. 21, 2013

Related U.S. Application Data

(60) Provisional application No. 61/329,593, filed on Apr. 30, 2010.

(51) Int. Cl.
*G01N 15/08*  (2006.01)
*G01N 5/04*  (2006.01)

(52) U.S. Cl.
CPC ............ *G01N 15/088* (2013.01); *G01N 5/04* (2013.01); *G01N 15/0806* (2013.01); *G01N 15/0893* (2013.01); *G01N 2015/086* (2013.01)

(58) Field of Classification Search
CPC .... G01N 5/04; G01N 15/0806; G01N 15/088; G01N 2015/086
(Continued)

(56) References Cited

U.S. PATENT DOCUMENTS 2,568,493 A * 9/1951 Garrison ...................... 236/1 R
2,679,159 A * 5/1954 Messer ............................ 73/38
(Continued)

FOREIGN PATENT DOCUMENTS

DE       3641821 A1 *  6/1988

OTHER PUBLICATIONS

R.H. Brown, "Pore Studies of Carbonate Aggregates by an Evaporation Technique," Joint Highway Research Project of the School of Civil Engineering, Purdue University, No. 22, Sep. 1968.*
(Continued)

*Primary Examiner* — Paul West
(74) *Attorney, Agent, or Firm* — Dorsey & Whitney LLP

(57) ABSTRACT

A method for determination of pore-size distribution in a porous material called evapo porometry (EP) is capable of determining pore sizes from approximately the nanometer scale up to the micron scale. EP determines the pore size based on the evaporative mass loss at constant temperature from porous materials that have been pre-saturated with either a wetting or non-wetting volatile liquid. The saturated porous material is placed in an appropriate test cell on a conventional microbalance to measure liquid mass loss at a constant temperature as a function of time. The mass-loss rate is then related to the pore-size distribution. The microbalance permits measuring the mass as a function of time. The slope of the mass versus time curve is the evaporation rate. The evaporation rate is related to the vapor pressure at the interface between the liquid in the porous
(Continued)

material and the ambient gas phase. The vapor pressure in turn is related to the pore diameter.

28 Claims, 18 Drawing Sheets

(58) Field of Classification Search
USPC .................................................. 73/38, 32 R
See application file for complete search history.

(56) References Cited

U.S. PATENT DOCUMENTS

| | | | |
|---|---|---|---|
| 2,913,897 A * | 11/1959 | Kirkham et al. | 73/38 |
| 3,939,698 A * | 2/1976 | De Lacy | 73/73 |
| 5,002,399 A * | 3/1991 | Akinc et al. | 374/14 |
| 6,319,736 B1 | 11/2001 | Baklanov et al. | |
| 6,789,410 B1 | 9/2004 | Gupta et al. | |
| 2004/0134933 A1 * | 7/2004 | Mutz et al. | 222/190 |
| 2009/0025894 A1 * | 1/2009 | Barnholtz et al. | 162/141 |

OTHER PUBLICATIONS

E.S. Messer, "Interstitial Water Determination by an Evaporation Method," AIME Petroleum Transactions, vol. 192, pp. 269-274, 1951.*

V.I. Balakhonova et al., "Investigation of the Process of Liquid Evaporation from a Porous Metal under Vacuum Conditions," Inzeherno-Fizicheskii Zhurnal, vol. 14, No. 1, pp. 48-54, 1968.*

K.S. Birdi, "Wettability and the evaporation rates of fluids from solid surfaces," J. Adhesion Sci. Technol. vol. 7, No. 6, pp. 485-493 (1993).*

Birdi et al., "Wettability and the Evaporation Rates of Fluids from Solid Surfaces," *Journal of Adhesion Science and Technology* (1993), 7(6):485-493.

International Search Report and Written Opinion dated Aug. 12, 2011, PCT/US2011/34853, 13 pages.

* cited by examiner

DETERMINATION OF PORE SIZE IN POROUS MATERIALS BY EVAPORATIVE MASS LOSS

CROSS REFERENCE TO RELATED APPLICATIONS

This application claims benefit under 35 U.S.C. §119(e) to U.S. Provisional Patent Application No. 61/329,593 filed 30 Apr. 2010 entitled "DETERMINATION OF PORE SIZE IN POROUS MATERIALS BY EVAPORATIVE MASS LOSS," which is hereby incorporated herein by reference in its entirety.

STATEMENT REGARDING FEDERALLY SPONSORED RESEARCH OR DEVELOPMENT

This invention was made with government support under grant number EEC0624157 awarded by the National Science Foundation. The government has certain rights in the invention.

TECHNICAL FIELD

The technology described herein is a technique and apparatus for determining the pore size and pore-size distribution of porous materials such as polymeric membranes, electrodes, adsorbents, and catalysts.

BACKGROUND

Accurate characterization of pore size and pore-size distribution is essential for the semi-permeable membranes that are used for applications such as water desalination, industrial gas separations, renal dialysis, membrane lung oxygenators, controlled-release drug delivery devices, and membrane-based sensors. In these applications the pore size determines the ability of the membrane to retain larger particles, bacteria, macromolecules, molecular aggregates, or molecules relative to the liquid or gas that permeates through the membrane. Such characterization is also required for porous electrodes used in batteries and fuel cells where the pore size determines the available surface area for charge transfer as well as for porous catalysts used in a variety of chemical processes where the pore size determines the available surface area for the heterogeneous catalytic reaction.

Several methods of characterizing the membrane pore-size distribution exist, and many have been well-reviewed. However, each technique is applicable to only a relatively limited range of pore sizes. For example, one can indirectly determine the pore-size distribution of a membrane by examining its rejection characteristics. Unfortunately, the solution for the pore-size distribution from sieving data is mathematically ill-posed without a unique solution. Gamma, lognormal, normal and Weibel-Rayleigh distribution functions have been used to fit the pore-size distribution data obtained from solute rejection, and observed that the area-averaged sieving coefficients are sensitive to the choice of the probability distribution functions. This could lead to uncertainty in the pore-size distribution obtained.

Microscopy techniques based on scanning electron microscopy (SEM), field-emission scanning electron microscopy (FESEM), and atomic force microscopy (AFM) have also been used to characterize pore structure. Microscopy techniques require expensive instruments that can measure only the pore size within a planar surface for a sample area of only a few hundred micrometers. As such, microscopy does not characterize the pore size throughout a porous sample of interest but rather provides a two-dimensional measure of a three-dimensional characteristic. Nonetheless, pore-size analysis based on microscopy provides important information regarding the pore-geometry, surface properties and anisotropy, which often play a major role in separation.

SEM requires skillful sample preparation to minimize artifacts due to drying and freeze-fracture that can often modify the original morphology and present a distorted presentation of the actual membrane structure. The use of AFM on membranes may cause the surface of the membrane to be distorted due to tip convolution. If the changes of height on the surface are of sufficient magnitude (>5 µm), contact may be lost between the tips and the sample. There is also often a discrepancy between pore sizes observed by microscopy and manufacturer-supplied pore-size ratings, mainly because the former is a direct measure of the pores on the membrane surface while the manufacturers report the size of particles retained by the membrane.

Mercury intrusion porosimetry measures the pressure required to force mercury into membrane pores. Both the volumes of through and blind pores are measured. However, this involves the use of high pressures with a toxic substance.

In capillary flow porometry (CAP), a non-reacting gas is passed through a dry sample, and then through the same sample after it has been wetted with a liquid. Based on the surface tension of the liquid and the difference in the pressures required, the size of the smallest neck in each pore can be determined. CAP measures the pore-throat diameter only, and does not give an indication of the pore volume.

U.S. Pat. No. 5,002,399 to Akinic describes another temperature-based technique for determining a material's porosity characteristics. In this technique, the porous material is saturated with a liquid, placed within an enclosed area, and then progressively heated by a furnace. As the temperature increases, the wetting liquid evaporates first from large diameter pores then from small diameter pores. The technique requires that both the temperature and mass of the material may be measured, and porosity is determined by measuring the change in mass as a function of temperature. In order to evaporate the liquid from pores with nm radii requires heating the material to temperatures exceeding 300° C. In addition to requiring a testing device that must accurately measure both temperature and mass within a closed environment, the high temperatures necessitated by this technique may alter the pore structure and/or degrade the porous material, thus, greatly limiting the types of membranes that can be tested.

Liquid displacement porometry (LDP) involves saturating the membrane with a wetting liquid and then gradually increasing the pressure of an immiscible fluid to cause displacement of the liquid progressively from the largest to the smallest pores as dictated by the Young-Laplace equation that relates the pore diameter to the pressure differential. The volume of pores of a given diameter can be determined from the flow rate if a model is assumed for the flow geometry. However, LDP is limited for characterizing ultrafiltration (UF) membranes owing to the high pressures required. For example, a UF membrane with a nominal pore size of 20 nm requires a pressure differential of 3.4 MPa to displace a wetting liquid having a surface tension of 15.9 mN/m. High pressures can cause compaction, thereby altering the membrane morphology.

Another pore-size characterization method for UF membranes is gas adsorption/desorption (GAD), which involves filling the pores via adsorption and capillary condensation by increasing the pressure of a gas. The pressure is then reduced to cause desorption of the liquid progressively from the largest to the smallest pores as dictated by the Kelvin equation that relates the pore diameter to the vapor pressure depression. The volume of pores of a given diameter can be determined from the volume of gas desorbed. GAD encounters limitations for larger pores owing to their smaller vapor-pressure reduction and limited accuracy in measuring the pressure and volume.

Thermoporometry involves freezing a liquid-saturated membrane and then gradually increasing the temperature to cause melting progressively from the largest to the smallest pores as dictated by the Gibbs-Thompson equation that relates the pore diameter to the freezing-point depression. The volume of pores of a given diameter is determined from the differential heat input. However, measuring this heat input with sufficient accuracy limits thermoporometry. In addition, a correction is required for the smallest pores owing to a submicron layer of unfrozen liquid at the pore walls that is caused by disjoining pressure effects.

Permporometry (PP) is a variation of GAD that involves simultaneous flow of a non-condensable gas that permits measuring only the continuous pores to the exclusion of the dead-end pores. PP is based upon filling the entire pore structure with a condensable gas, and subsequently removing this gas by progressively lowering its partial pressure. As the pressure is reduced, pores having a size corresponding to the vapor pressure applied are emptied, and become available for gas transport. The vapor pressure is related to the pore size by the Kelvin equation. Maintaining equal pressures on both sizes of the membrane to avoid pressure-driven flow during desorption is difficult, and a correction must be made to the data to account for the adsorbed monolayer that remains in each pore after desorption. PP is subject to the same limitations as GAD. Moreover, the required control of the gas partial pressure is difficult.

Ultrasonic reflectometry has demonstrated significant capability as a real-time, non-destructive and non-invasive tool for characterizing various membrane processes. Ultrasonic spectroscopy using highly sensitive piezoelectric transducers has been employed to study the acoustic properties of polymer membranes and relate them to their filtration characteristics. General trends between velocity and membrane properties have been described, as well as relationships between the acoustic properties to actual pore characteristics. The application of ultrasonic reflectometry has been broadened to accommodate the non-invasive characterization of membrane morphology including defect detection. However, pore-size determination in this case does not represent a primary measurement, but rather reflects a statistical fit to a known distribution.

Overall, there is no one technique that is capable of determining pore sizes ranging from nanometer to the micrometer scale, the range of interest in membrane applications. Techniques such as DP require relatively expensive dedicated equipment that involves the application of high pressures that can deform the material being studied. Moreover, DP can characterize only relatively large pores that are typically larger than 10 nm. Techniques such as gas adsorption/desorption also require relatively expensive dedicated equipment that involves measuring the gas pressure very accurately. Moreover, gas adsorption/desorption relies on a phenomenon known as capillary condensation whereby pores fill by progressive adsorption. For this reason, gas adsorption/desorption can accurately characterize only relatively small pores, i.e., typically less than 10 nm. Techniques such as SEM and AFM require expensive instrumentation that can measure only the pore size within a planar surface for a sample area of only a few hundred micrometers. As such, microscopy does not characterize the pore size throughout a porous sample of interest. Other less commonly used pore-size characterization techniques such as TP and PP also require dedicated relatively expensive equipment and are difficult to implement reliably.

The information included in this Background section of the specification, including any references cited herein and any description or discussion thereof, is included for technical reference purposes only and is not to be regarded subject matter by which the scope of the invention is to be bound.

SUMMARY

A method for determination of pore-size distribution is referred to herein as evapoporometry (EP). This technique is capable of determining pore sizes over the full range of interest, which is typically from approximately the nanometer scale up to the micrometer scale. EP determines the pore size based on the evaporative mass loss from porous materials in an open test cell at constant temperature, where the material has been pre-saturated with either a wetting or non-wetting volatile liquid.

EP is based on evaporating a wetting volatile liquid from a membrane under conditions for which the gas at the membrane surface is saturated with respect to the liquid in the pore size that is draining, but supersaturated with respect to all smaller pores. Hence, evaporation will progress from the largest to the smallest pores. The principle underlying this technology is that the vapor pressure will be reduced for wetting liquids, whereas it will be increased for non-wetting liquids owing to the effects of surface curvature at the interface of a liquid within pores. A porous material that has been saturated with a volatile liquid in an appropriate test cell is placed on a conventional microbalance to measure mass loss as a function of time from a wetted porous material; the mass-loss rate is then related to the pore-size distribution. The microbalance permits measuring the mass as a function of time.

The slope of the mass versus time curve is the evaporation rate. The evaporation rate can be related to the vapor pressure at the interface between the liquid in the porous material and the ambient gas phase. The vapor pressure in turn can be related to the pore diameter. If the porous material is pre-saturated with a wetting, volatile liquid, the evaporation rate will monotonically decrease as a function of time. This is because the liquid will evaporate progressively from the largest pores down to the smallest pores since the vapor pressure decreases with decreasing pore diameter for a wetting liquid. At any instant of time, liquid will be evaporating from only one pore size since the ambient gas phase environment above any smaller pores will be supersaturated, whereas any larger pores will already have been emptied.

In one implementation, an apparatus for determining pore size in a porous material uses a test cell formed as a diffusion chamber placed upon a microbalance. The porous material sample is affixed to a bottom of the test cell and a seal structure positioned about the porous material sample to prevent lateral liquid and vapor loss. A volume of a volatile liquid is introduced within the test cell on an upper surface of the porous material sample. Measurements of mass loss from evaporation of the liquid are taken over time. The evaporation rate is related to a vapor pressure at an interface between the volatile liquid in the porous material sample and an ambient gas phase within the test cell and the vapor pressure can be related to a pore diameter.

In another implementation, a method of characterizing a porous material is disclosed. The method may comprise wetting the material in a volatile liquid, placing the material in a test cell, covering the material with a volatile liquid, positioning the test cell on a microbalance within an environmental chamber, and measuring the change in mass of the test cell under isothermal conditions over time.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. A more extensive presentation of features, details, utilities, and advantages of the present invention is provided in the following written description of various embodiments of the invention, illustrated in the accompanying drawings, and defined in the appended claims.

DETAILED DESCRIPTION

Figure 1:
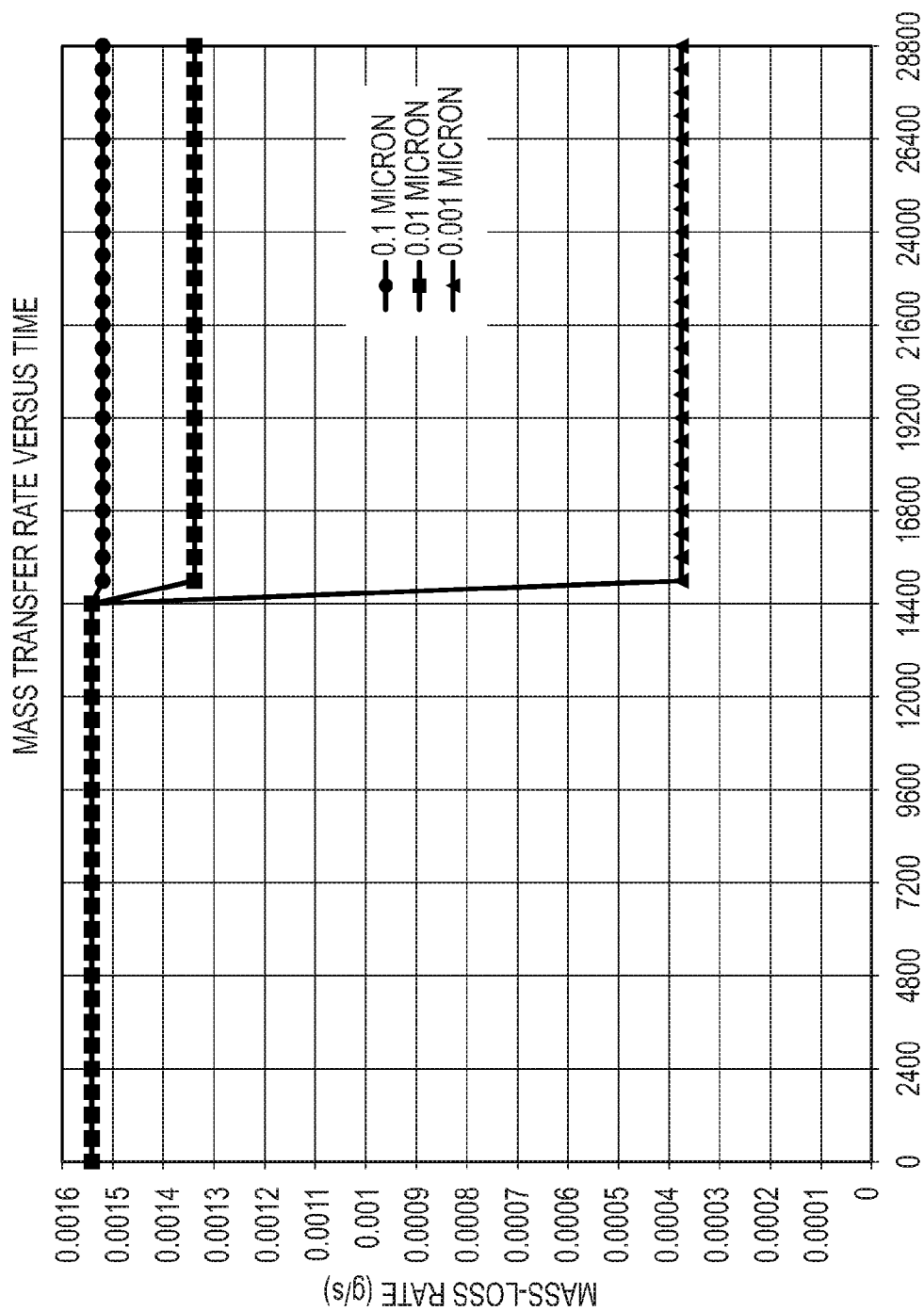
FIG. 1 is a graphical plot of a simulated mass-loss rate (g·s$^{-1}$) versus time (s) results for the evaporation of a free-standing isopropanol (IPA) layer and subsequent evaporation from the pores of ideal membranes that contain pores that are either 0.1, 0.01, and 0.001 μm in diameter.

It is often necessary to characterize the pore size and pore-size distribution in a variety of applications. For example, it is necessary to accurately characterize the pore size and pore-size distribution for semi-permeable membranes that are used for applications such as water desalination, industrial gas separations, renal dialysis, membrane lung oxygenators, controlled release drug delivery devices, and membrane sensors. In these applications the pore size determines the ability of the membrane to retain larger particles, bacteria, macromolecules, molecular aggregates, or molecules relative to the liquid or gas that permeates through the membrane. It is also necessary to characterize the pore size and pore-size distribution for porous electrodes used in batteries and fuel cells. In these applications the pore size determines the available surface area for charge transfer. Other applications of this invention include determining the pore size and pore-size distribution in porous catalysts used in a variety of chemical processes. In these applications the pore size determines the available surface area for the heterogeneous catalytic reaction.

Techniques for determining pore size such as displacement porometry require relatively expensive dedicated equipment that involves the application of high pressures that can deform the material being studied. Moreover, displacement porometry can characterize only relatively large pores typically greater than 0.01 μm. Techniques such as gas adsorption/desorption also require relatively expensive dedicated equipment that involves measuring the gas pressure very accurately. Moreover, gas adsorption/desorption relies on a phenomenon known as capillary condensation whereby pores fill by progressive adsorption. For this reason gas adsorption/desorption can accurately characterize only relatively small pores typically less than 0.01 μm.

Techniques such as scanning electron microscopy (SEM) require a very expensive instrument that can measure the pore size only within a planar surface that may have a sample area as small as only a few hundred square micrometers. As such, SEM does not characterize the pore size throughout a porous sample of interest but rather provides a two-dimensional measure of a three-dimensional characteristic whereby the pore size may not be representative. Other less commonly used pore-size characterization techniques such as thermoporometry and permporometry also require dedicated relatively expensive equipment and are difficult to implement reliably.

In contrast, as described herein, evapoporometry determines the pore size based on the evaporative mass loss from porous materials that have been pre-saturated with wetting volatile liquid. Evapoporometry uses a conventional microbalance to measure the mass loss as a function of time from the porous material that is contained with an appropriately designed test cell. Moreover, evapoporometry permits characterizing pore size from a few nanometers up to near micrometer scale, a range of particular practical interest.

Evapoporometry Theory

Evapoporometry is based on evaporating a wetting volatile liquid from a membrane under conditions for which the gas at the membrane surface is saturated with respect to the liquid in the pore size that is draining, but supersaturated with respect to all smaller pores. Hence, evaporation will progress from the largest to the smallest pores. The principle underlying the evapoporometry method is that the vapor pressure will be reduced for the wetting liquids. This method involves placing a porous material that has been saturated with a volatile liquid in an appropriate test cell that in turn is placed on a microbalance, which enables measuring the mass as a function of time. The slope of the mass versus time curve provides the evaporation rate, which can be related to the vapor pressure at the interface between the liquid in the porous material and the ambient gas phase. The vapor pressure in turn can be related to the pore diameter.

If the porous material is pre-saturated with a wetting volatile liquid, the evaporation rate will monotonically decrease as a function of time. This rate change occurs because the liquid will evaporate progressively from the largest pores to the smallest pores since the vapor pressure decreases with decreasing pore diameter for a wetting liquid. At any instant of time, liquid will be evaporating from only one pore size since the ambient gas-phase environment above any smaller pores will be supersaturated, whereas any larger pores will already have been emptied. The fundamental assumptions for the EP method are that the testing liquid is incompressible, and that the Kelvin equation can be applied to quantify the effect of curvature on vapor pressure.

A. Application of the Kelvin Equation

In order to obtain a pore-size distribution, the Kelvin equation may be applied with the following assumptions: isothermal conditions, one-dimensional diffusion, quasi-steady state conditions with minimum end effects, and constant binary diffusion. It may also be assumed that the liquid draining at any time arises from pores characterized by their diameter as viewed from the upper surface of the membrane. In fact, when interconnecting or tapered pores are present, liquid is also draining from interfaces within the membrane. This causes an inaccuracy in the number of pores of a given size. In addition, an assumption is made that lateral diffusion is rapid so that local supersaturation is maintained above any pores smaller than the ones that are draining at any given time.

The relation between the vapor pressure and the pore size is given by:

$$\ln \frac{\overline{p_A}}{p_A^0} = -\frac{4\sigma \cos\theta V}{RTd} \tag{1}$$

where $\overline{p_A}$ is the vapor pressure at any point in time (Pa), $p_A^0$ is the vapor pressure of a surface or free-standing liquid (Pa), σ is the surface tension of the liquid (Nm$^{-1}$), θ is the contact angle, V is the molar volume of the liquid (m$^3$), R is the gas constant ($JK^{-1}$ $mol^{-1}$), T is the absolute temperature (K), and d is the mean diameter of the pore (m). Note that if d is infinite corresponding to a planar interface between the volatile liquid and ambient gas phase, equation (1) indicates that the partial pressure will be equal to the equilibrium vapor pressure. However, if d<∞, equation (1) indicates that the partial pressure will be less than the equilibrium vapor pressure for a planar interface.

B. Equations Used in Calculations

The evaporation rate is a unique function of the diameter of the pores from which liquid is evaporating at any given time. The vapor pressure of the pores draining at any time is determined from the instantaneous evaporation rate, which in turn is determined from the mass loss recorded by the microbalance. The vapor pressure at any point in time and the vapor pressure of the surface or free-standing liquid may be calculated using the following equations:

$$p_A^0 = p_T \left(1 - e^{\frac{W_0 L}{cD_{AB} S_c}}\right) \quad (2)$$

$$\overline{p_A} = p_T \left(1 - e^{\frac{WL}{cD_{AB} S_c}}\right) \quad (3)$$

where $p_T$ is the atmospheric pressure (Pa), $W_0$ is the evaporation rate of the surface or free-standing liquid ($mols^{-1}$), W is the evaporation rate of liquid from pores ($mols^{-1}$), L is the length of the diffusion path (m), c is the molar density of vapor ($molm^{-3}$), $D_{AB}$ is the binary diffusion coefficient ($m^2s^{-1}$), and $S_c$ is the cross-section area of the test cell ($m^2$). The diameter of the pores draining at any time is a unique function of the instantaneous vapor pressure as determined by the Kelvin equation (equation 1). Hence, in this manner the pore size and pore-size distribution of a membrane sample can be determined.

For example, if an ideal membrane containing pores of only one size is assumed, then a plot of mass-loss rate as a function of time will evidence only one particular value of mass-loss rate. The horizontal line that corresponds to this particular value of mass-loss rate will extend over a time period sufficient to encompass evaporation of liquid from all of the pores of this one size. This mass-loss rate value corresponds to the particular value of vapor pressure that can be related (via the Kelvin equation) to a particular pore-size diameter under the specific experimental conditions.

C. Test Cell Design Considerations

The vapor pressure in Eq. (1) is obtained from the evaporation rate in a vented diffusion chamber, described in detail below. The diffusion chamber is placed on a microbalance equipped with temperature and humidity sensors and a polonium source to mitigate static charging. The microbalance is placed in a constant-temperature environmental chamber that rests on an anti-vibration table. The membrane is saturated and overlain with a thin layer of a wetting non-interacting volatile liquid. The vapor diffuses upward from the liquid layer interface. After the liquid layer has evaporated, evaporation begins from only the largest pores, since the gas at the membrane surface is supersaturated with respect to the smaller pores. When the largest pores are empty, evaporation commences from the next largest pores. The liquid is evaporated from progressively smaller pores until all pores are empty. The relationship between $p'_A$ and the evaporation rate $W_A$, determined from the microbalance, is obtained from the solution to the species-balance equation in the diffusion chamber.

C.1. Solution of Species-Balance Equation

The steady-state one-dimensional species balance for the diffusing vapor of the volatile liquid used to saturate the membrane is given by $$\frac{dN_A}{dz} = 0 \quad (4)$$

where z is a spatial coordinate measured upward from the surface of the membrane and $N_A$ is the molar flux of component A relative to a stationary reference frame described by Fick's law of diffusion given by $$N_A = -cD_{AB} \frac{dy_A}{dz} + y_A N_A \quad (5)$$

where c is the molar density of the gas, $D_{AB}$ is the diffusion coefficient and $y_A$ is the mole fraction of the vapor resulting from the volatile liquid. Eq. (5) includes the bulk flow term required when the gas-phase concentration is not necessarily small. Eqs. (4) and (5) require two boundary conditions:

$$y_A = \frac{p'_A}{P} \text{ at } z = 0 \quad (6)$$

$$y_A = 0 \text{ at } z = L \quad (7)$$

Eq. (6) specifies that $y_A$ is determined by its vapor pressure $p'_A$ at the membrane surface and the total pressure P. Eq. (7) specifies that $y_A$ is zero at the open end of the diffusion chamber at a distance L from the membrane surface. Integration yields $$N_A = -\frac{cD_{AB}}{L} \ln\left(1 - \frac{p'_A}{P}\right) \quad (8)$$

Eq. (8) can be recast in terms of the evaporation rate $W_A = N_A S_c$ where $S_c$ is the cross-sectional area of the membrane:

$$W_A = -\frac{cD_{AB} S_c}{L} \ln\left(1 - \frac{p'_A}{P}\right) \quad (9)$$

C.2. Justification of Model Assumptions

Solving the species balance uncoupled from the thermal energy equation implies that the evaporation is isothermal. This assumption is checked by determining whether the vapor pressure obtained from the evaporation rate for the liquid layer initially on the membrane corresponds to the value for the ambient temperature. Assuming one-dimensional mass transfer requires that the time for diffusion between adjacent pores be much shorter than that for mass transfer through the diffusion chamber. This translates to the distance between adjacent pores being much less than the length of the diffusion chamber:

$$\frac{1-\varepsilon}{nL^2} \ll 1 \quad (10)$$

where $\varepsilon$ is the porosity and n is the number of pores per unit area. The evaporation process is unsteady-state owing to the initial transient when the concentration profile of the diffusing vapor is established and because the thickness of the liquid layer on the membrane decreases in time. The criteria for assuming steady-state have been determined via systematic scaling analysis by Krantz (Scaling Analysis in Modeling Transport and Reaction Processes—A Systematic Approach to Model Building and the Art of Approximation, Wiley, New York, 2007):

$$\frac{D_{AB}t}{L^2} \gg 1 \text{ and } V_A C \ll 1 \tag{11}$$

where t is the contact time and $V_A$ is the molar volume of the volatile liquid. An end effect is encountered owing to diffusion of vapor from the cylindrical diffusion chamber into the ambient air. The latter can be modeled as diffusion from a circular plate into its unbounded surroundings, which can be obtained from the solution for heat conduction from a circular plate into its unbounded surroundings given by Carslaw and Jaeger (Conduction of Heat in Solids, Oxford University Press, 3rd ed., Oxford, 1959) using the analogy between heat and mass transfer (Int. J. Heat Mass Transfer 22, 469 (1979)). The criterion for ignoring this end effect reduces to demanding that the ratio of the mass-transfer resistance of the end effect be small in comparison to that of the diffusion chamber that can be obtained from Eq. (9); that is, $$\frac{\pi d}{8L} \ll 1 \tag{12}$$

where d is the diameter of the diffusion chamber.

In various embodiments the test cell may have boundary conditions other than those described above. In one embodiment the test cell may be formed with a lid having a vent hole. In such an embodiment a solution for the mass-transfer resistance within the chamber (i.e. test cell), and a solution for the mass-transfer resistance may be developed which include an exit effect created by the vent hole. Where the test cell has a base diameter of $d_1$, vent hole diameter of $d_2$ and a length L filled with evaporative liquid, and if z is the distance from the surface of the liquid, then the simplified species balance equation for the test cell with a vent hole is given by:

$$0 = \frac{d^2 c_A}{dz^2} \tag{A}$$

where $c_A$ is the concentration of the evaporative liquid. This equation assumes the use of dilute solutions so that the bulk flow effect can be ignored, constant binary diffusion coefficient, and quasi-steady-state conditions such that the motion of the liquid-gas interface can be ignored.

The boundary conditions on this equation are: $c_A = c_A^o$ at z=0 and $c_A = c_{AL}$ at z=L. The solution to equation (A) subject to the boundary conditions is:

$$c_A = c_A^o - \frac{c_A^o - c_{AL}}{L} z \tag{B}$$

The corresponding mass-transfer evaporative flux ($N_A$) is given by:

$$N_{Az} = -D_{AB} \frac{dc_A}{dz} = D_{AB} \frac{c_A^o - c_{AL}}{L} \tag{C}$$

and the corresponding mass-transfer evaporation rate ($W_A$) is given by:

$$W_A = N_A \pi \frac{d_1^2}{4} = \pi D_{AB} \frac{d_1^2}{4} \frac{c_A^o - c_{AL}}{L} \tag{D}$$

Hence, the resistance to mass transfer within the test cell is:

$$R_1 = \frac{c_A^o - c_{AL}}{W_A} = \frac{4L}{\pi D_{AB} d_1^2} \tag{E}$$

The equation for the mass flux from a semi-infinite space towards a circular disk can be obtained from the solution to an analogous heat-transfer problem, and is given by:

$$N_{Az} = \frac{8 D_{AB}}{\pi d_2} (c_{AL} - c_{A\infty}) \tag{F}$$

The corresponding mass-transfer rate is given by:

$$W_A = N_{Az} \frac{\pi d_2^2}{4} = 2 D_{AB} d_2 (c_{AL} - c_{A\infty}) \tag{G}$$

and the resistance to mass transfer at the inlet of the vent hole is:

$$R_2 = \frac{c_{AL} - c_{A\infty}}{W_A} = \frac{1}{2 D_{AB} d_2} \tag{H}$$

Note that the total resistance to mass transfer includes two contributions at the vent hole: one for the entrance, and the other for the exit. Thus, the total resistance to mass transfer for the test cell and vent hole is:

$$R_T = R_1 + 2 R_2 = \frac{4L}{\pi D_{AB} d_1^2} + \frac{1}{D_{AB} d_2} \tag{I}$$

Hence, the rate of mass transfer from the vented test cell is given by:

$$W = \frac{c_A^o - c_{A\infty}}{\frac{4L}{\pi D_{AB} d_1^2} + \frac{1}{D_{AB} d_2}} \tag{J}$$

Since the mass-transfer rate is to be controlled by the diffusion within the test cell, the following criterion must be satisfied:

$$\frac{4L}{d_1^2\pi} \geq \frac{1}{d_2} \Rightarrow \frac{d_2}{d_1} \geq \frac{d_1\pi}{4L} \quad (K)$$

The above criterion cannot be satisfied unless a sufficiently deep (very large L) test cell is used. For example, the largest that $d_2$ can be is equal to $d_1$; even for this case L would be required to have a length greater than $10 \times d_1$. However, note that equation (G) indicates that the mass-transfer rate is directly proportional to $c_{AL}-c_{A\infty}$ irrespective of which resistance is controlling.

One of skill in the art will recognize that differently shaped test cells may be used by modifying the boundary conditions described above.

D. Evapoporometry Calculations for an Ideal Membrane

If the volume of the dry sample is measured, the mass of evaporating liquid is determined, and the density of the liquid is known, then the porosity can be calculated by converting the evaporating mass to a total pore volume and then dividing by the total sample volume. If an ideal membrane containing pores of only one size is assumed, then a plot of mass-loss rate as a function of time will evidence only one particular value of mass-loss rate. The horizontal line that corresponds to this particular value of mass-loss rate will extend over a time period sufficient to encompass evaporation of liquid from all of the pores of this one size. This mass-loss rate value corresponds to the particular value of vapor pressure that can be related (via the Kelvin equation) to a particular pore-size diameter under the specific experimental conditions.

In order to assess the limitations of the EP technique for determining the membrane pore size and pore-size distribution, calculations may be made for three idealized membranes having a porosity of 50% and pore diameters of 0.1, 0.01, and 0.001 μm, respectively. These calculations involve determining (1) the time required to evaporate a free-standing isopropanol (IPA) layer; (2) the time required to evaporate all of the IPA from the aforementioned membranes for a sample having a diameter of 5.6 cm and a thickness of 150 μm, and (3) simulated mass-loss rate versus time data for each membrane.

Assume that the free-standing IPA layer involves 100 droplets, each of which has a diameter of 0.1 cm. With an IPA density of 0.788 gcm$^{-3}$, we will have a mass:

$$m = (100)\frac{4}{3}\pi r^3 \rho = (100)\frac{4}{3}\pi (0.05 \text{ cm})^3 (0.788 \text{ g/cm}^3) = 4.13 \times 10^{-2} \text{ g} \quad (15)$$

The evaporation rate determined experimentally for free-standing IPA at 303 K is $W_0=2.57\times10^{-6}$ gs$^{-1}$; hence, the time required to evaporate this free-standing IPA is 4.46 h. The evaporation rate from a membrane with a given pore size will be equal to the evaporation rate from a free-standing IPA layer multiplied by the ratio of its reduced vapor pressure to the normal vapor pressure; that is:

$$W = W_0 \frac{\overline{p_A}}{p^0} \quad (16)$$

The reduced vapor pressure in turn is determined from the Kelvin equation as follows:

$$\ln \frac{\overline{p_A}}{p^0} = \quad (17)$$

$$-\frac{2\sigma V}{rRT} = \frac{2(23 \text{ gs}^{-2})(76.3 \text{ cm}^3 \text{ mol}^{-1})}{r(82.06\times10^6 \text{ cm}^2 \text{ gmol}^{-1}\text{Ks}^2)(303 \text{ K})} = -\frac{1.41 \times 10^7}{r}$$

Then $\overline{p_A}/p_0$ is 0.986 for 0.1 μm pores, 0.868 for 0.01 μm pores, and 0.244 for 0.001 μm pores. Using equation (16), the evaporation rate (W) for each of the above pore sizes is: $2.53\times10^{-6}$ g·s$^{-1}$ for 0.1 μm pores, $2.23\times10^{-6}$ g·s$^{-1}$ for 0.01 μm pores, and $6.27\times10^{-7}$ g·s$^{-1}$ for 0.001 μm pores.

Now, if we assume that a single membrane disk having a diameter of 5.6 cm, a thickness of 150 μm, and a porosity of 50% is placed in the test cell, the mass of IPA in the pores of this membrane is given by:

$$m=(0.50)4\pi r_m^2 L\rho=(0.50)4\pi(2.8 \text{ cm})^2(150\times10^{-4} \text{ cm})$$
$$(0.788 \text{ g/cm}^3)=0.582 \text{ g} \quad (18)$$

The time required to evaporate the IPA from the pores for each of the three membranes is calculated to be: 63.9 h for 0.1 μm pores, 72.5 h for 0.01 μm pores, and 257 h for 0.001 μm pores. These time periods are long enough to obtain sufficient data to characterize these three pore sizes via EP. We will assume that it takes 14,400 s to evaporate the free-standing IPA layer before the pores begin to drain. Simulated mass-loss rate versus time results for all three membranes are presented in FIG. 1. The point at which IPA begins to evaporate from the 0.1 μm pores cannot be easily discerned. In contrast, the point at which the 0.01 and 0.001 μm pores begin to drain is easily detected. Clearly, mass-loss rate provides a more discriminating way to determine the onset of evaporation from all three membranes. The estimated error in determining the mass-loss rate is $1.4\times10^{-6}$ g·s$^{-1}$; hence, the error bars would not be seen on the scale of FIG. 1.

Methodology

EP methodology development focused on the design of a suitable test cell for the porous substrate of interest, identification and control of the essential testing parameters, and an analysis protocol that minimized experimental uncertainty. Critical experimental considerations included the ability to achieve one-dimensional diffusion, minimize end effects, and continuously make mass measurements with high accuracy over a reasonably long period of time. In addition, EP experiments required careful control of temperature, minimizing any effects of mechanical vibration or electrostatic charging due to dry ambient conditions. The test cell was designed in such way as to eliminate any lateral vapor or liquid leakage. Testing liquids were selected on the basis of compatibility with the membrane material as well as a vapor pressure high enough to minimize the time required for characterization. Membrane materials with well-characterized pore geometry were selected, results were compared with well-established techniques for characterizing pore-size distribution.

A. Membrane Samples and Test Liquids

Track-etched polycarbonate Nuclepore membrane samples (e.g., GE Osmonics Labstore, Minnetonka, Minn.) of five different nominal pore diameters: 10, 30, 50, 100 and 200 nm were tested. Nuclepore membrane samples used here were flat disks having a diameter of 47 mm. All of these membrane samples have a thickness of approximately 6 μm, except for the 200 nm membrane, which is 10 μm thick.

The membranes were cut to a diameter of 4.7 cm to fit into the recess in the base plate of the diffusion chamber. As described more fully in the Examples, the accuracy of evapoporometry was assessed by characterizing membranes used as standards because of their relatively regular pore structure and narrow pore-size distribution. Nuclepore™ (GE Osmonics Labstore) track-etched polycarbonate membranes, approximately 6 μm thick, having nominal pore diameters of 10, 50 and 100 nm, and Anopore™ (e.g., Whatman, Maidstone, UK) aluminum oxide membranes having nominal pore diameters of 20 and 100 nm were used. Nuclepore™ membranes have cylindrical, non-interconnected pores that are created by exposing a polycarbonate film to radiation that alters the polymer structure to create areas that can be removed by acid etching. Anopore™ membranes are created via electrochemical deposition of alumina that creates a support layer of nominal 200 nm columnar, non-interconnected pores approximately 55 μm thick upon which a thin layer of smaller interconnected pores approximately 5 μm thick is deposited.

The membranes were also characterized using either low-vacuum SEM (JEOL model JSM-6480LV) or FESEM (JEOL model JSM-7401F) on at least three random areas on each membrane sample. The samples were coated with 2 nm of Au/Pd (60:40) with a sputter-coater (Cressington Scientific Instruments model 108). Equivalent cylindrical pore diameters were obtained using image analysis software (SigmaPlot SigmaScan).

All membrane samples except Nuclepore 10 nm were characterized by imaging micrographs obtained by low-vacuum SEM (e.g., model JSM-6480LV, JOEL Ltd., Japan). Nuclepore 10 nm membrane samples were imaged with a field-emission scanning acoustic microscopy (FESEM) (e.g., model JSM-7401F, JOEL Ltd., Japan). At least three random microscopic fields on one membrane sample were chosen for imaging. For image analysis, the surface of the membrane samples was coated with a 2 nm layer of a Au/Pd (ratio 60:40) with an auto sputter coater (e.g., model 108, Cressington Scientific Instruments Ltd., Watford, UK). Image analysis is performed by SigmaScan (e.g., SigmaPlot, San Jose, Calif.) image analysis software. The brightness of the micrographs was adjusted manually to obtain the best contrast for accurate image analysis. The image analysis software employed the measurement of an equivalent pore diameter, i.e., the diameter of a circle of equal area as the pore of interest.

Histological-grade isopropyl alcohol (Mallinckrodt Chemicals) was used as the wetting, non-interacting, volatile liquid. Its surface tension of 23.00 mN/m and vapor pressure of 30.93 torr at 20° C. permitted characterizing the pore-size distribution accurately within 1.4 hours. Classical methods such as LDP take comparable or slightly longer time since they require slowly increasing the pressure from atmospheric to that required to displace the liquid from the smallest pores while measuring the volume flow at each pressure to obtain the pore-size distribution. For example, LDP characterization of the 20 nm PVDF membrane required using pressures over 3 MPa and took approximately three hours.

EP measurements were conducted using different testing liquids. In addition to the criteria noted above, a critical requirement was that the liquid exhibit evaporation characteristics that include a well-defined baseline with small noise levels and a minimum curvature. Two testing liquids were selected: isopropanol (IPA) and n-propanol (NPA).

B. Equipment and Experimental Protocol

Figure 2:
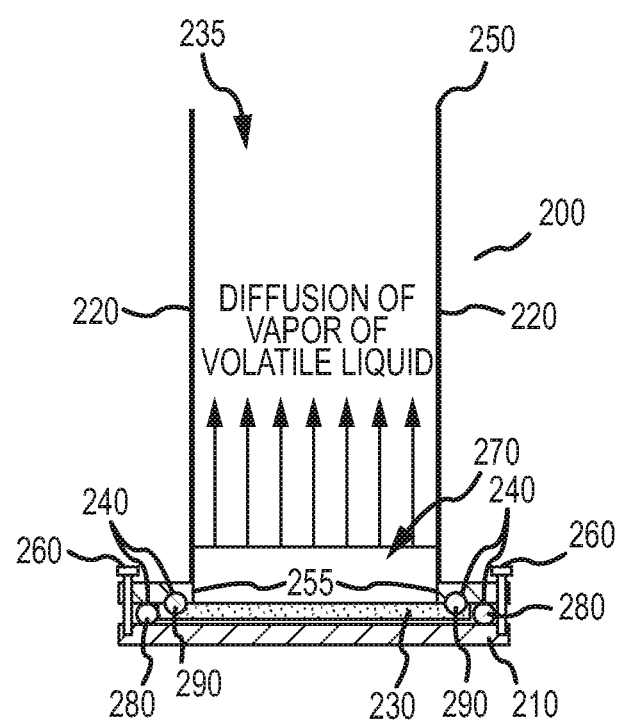
FIG. 2 is a schematic diagram of an implementation of a test cell design that secures the membrane sample by direct compression and employs two O-rings to eliminate any lateral loss of volatile liquid or vapor.

As shown in FIG. 2, an exemplary test cell 200 was fabricated from aluminum and consists of a two parts: a base 210 and an upper portion 220. In this exemplary test cell 200, the base 210 is a 77 mm diameter plate (bottom) that connects to the upper portion, formed as a 10.5 mm long cylinder (top). The bottom or base plate 210 may be milled to create a recess to accommodate a specific diameter membrane 230, for example a 4.7 cm diameter membrane. The membrane 230 may be sealed against lateral leakage by two O-rings 240, one seated in or on the lower base 210, and the other O-ring positioned in the upper portion 220. The O-rings may be positioned such that one O-ring has a larger diameter than the other, the O-ring with the larger diameter may be referred to as an outer O-ring 280, and the smaller O-ring referred to as the inner O-ring 290. The outer O-ring 280 may be positioned in the lower plate 210 to aid in sealing against liquid or vapor loss beneath the membrane 230 sample. Before each test, the membrane 230 sample was wetted by immersing it in the testing liquid for at least 4 hours. The fully-wetted membrane 230 sample is then placed on the lower base plate 210 of the test cell 200. The upper portion 220 of the test cell 200 was then placed over the lower plate 210 and connected by a securing assembly 260, for example six hexagonal nuts positioned about the upper portion 210. The nuts of the securing assembly may be tightened using a torque wrench at a pressure of 38 kPa to ensure that the same pressure was applied over the whole membrane sample surface. A volatile liquid 270 may be layered over the membrane 230, which may be accessible through a lower opening 255 in the upper portion 220 of the test cell 200. Vapor of the volatile liquid 270 may diffuse upward through an interior 235 of the upper portion 220. Diffusion of the volatile liquid vapor is shown with arrows in FIG. 2. The vapor may exit the test cell 200 at an upper opening 250 in the upper portion 220. In several embodiments, the upper opening 250 and the lower opening 255 may have the same diameter, for example, where the interior 235 of the upper portion 220 forms a cylinder of constant diameter. In other embodiments, the upper opening 250 may be smaller than the lower opening 255, such as wherein the embodiment includes a lid positioned atop the upper portion 220, the lid forming a vent hole with a diameter less than the diameter of the lower opening.

In various other embodiments the interior 235 of the upper portion 220 may form other than a cylinder, for example a square cross-sectional upper portion, with accompanying modifications to the boundary conditions described above.

Figure 3:
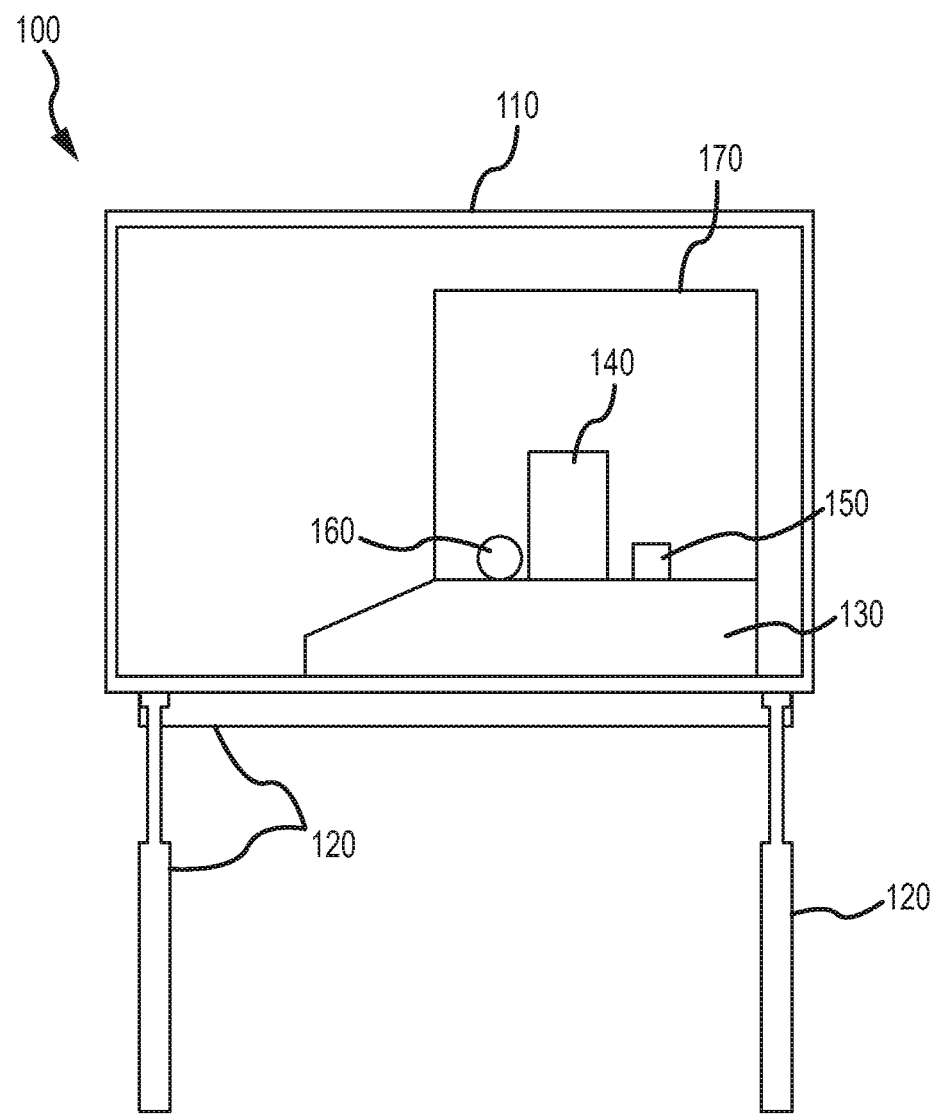
FIG. 3 is a schematic diagram of an exemplary implementation of an evapoporometry (EP) testing arrangement. The microbalance rests on a shelf in a low-temperature environmental chamber operated under isothermal conditions. The microbalance is situated on an anti-vibration table. A polonium source to mitigate static charge and a temperature sensor are located inside the microbalance chamber.

The test cell containing the membrane sample was then placed on a microbalance (e.g., model ME235S, Sartorius, Goettingen, Germany) mounted in a low-temperature environmental chamber (e.g., model IE75-4A, So-Low Environmental Equipment Co., Inc., Cincinnati, Ohio) that is situated on an anti-vibration table as shown in FIG. 3.

As shown in FIG. 3, an experimental apparatus 100, comprises an environmental chamber 110 positioned atop an anti-vibration platform 120. In some embodiments, such as that shown in FIG. 3, the anti-vibration platform may be a table. A microbalance 130, test cell 140, static-charge mitigation source 150, and temperature and humidity sensor 160 are positioned within the environmental chamber 110. In various embodiments the static-charge mitigation source 150 may be a polonium source. In further embodiments other weak radiation sources could be used to mitigate static charging. In various embodiments, the environmental chamber may be designed to accommodate variously sized test cells.

The microbalance 130, which may permit measuring the mass as a function of time. In one particular embodiment used to generate the data herein, the microbalance has a weighing capacity of 230 g with a repeatability of 30 μg. In other embodiments, the microbalance may be designed or chosen to have a weighing capacity, repeatability, and tare limit to accommodate a specific size of test cell. Here the repeatability of the microbalance 130 is defined as the ability to consistently deliver the same mass reading and to return to zero after each weighing cycle. The microbalance must have a resolution of at least 100 micrograms or less and the ability to tare out the mass of the test cell, which may be between 100 and 200 grams. In some embodiments the test cell mass may be more than 200 grams or less than 100 grams and the microbalance will have a resolution and tare limit to accommodate such a test cell. In various embodiments the microbalance may be chosen to accommodate a specifically dimensioned test cell. For example, a large test cell may require a microbalance with a larger weighing surface to accommodate the test cell. In many embodiments the temperature within the environmental chamber 110 may be controlled to within one degree Celsius. In some embodiments, the temperature sensitivity factor of an exemplary microbalance is $\leq \pm 10^{-6}$ per K. Before each experiment the microbalance may be calibrated using the internal calibration function with built-in motorized calibration weights.

As shown in FIG. 3, the test cell 140, which is formed as a diffusion chamber, is positioned on the microbalance 130 so that the mass of the test cell can be monitored over time. The static-charge mitigation source 150 may mitigate static charging within the environmental chamber, and the temperature and humidity sensor 160 may aid in monitoring and controlling the temperature within the environmental chamber 110. In various embodiments the microbalance 130 may have a visual and/or electronic readout. In some embodiments the electronic readout of the microbalance may be transmitted to a memory device which may record and store the mass from the microbalance 130 as a function of time. The memory device may also record and store temperature and humidity readings from the temperature and humidity sensor 160. In various embodiments the memory device may be functionally connected to or part of a computational or processing unit, for example a computer.

In an exemplary embodiment, the mass data may be recorded and logged via RS232 data-acquisition software (e.g., Win Wedge, TAL Technologies, Inc., Philadelphia, Pa.) into a laboratory computer every 10 s. The polonium source (e.g., model Staticmaster 2U500, NRD LLC, Grand Island, N.Y.) may be located inside a microbalance chamber 170 to aid in mitigating static charging. The temperature sensor 160 (e.g., model HOBO® U12, Onset, Bourne, Mass.) was also located in microbalance chamber. A testing liquid (0.8 mL) is then carefully added (to avoid wetting the sides of the test cell) with a plastic syringe to create a thin layer of freestanding liquid over the entire membrane sample. The test cell 140 and microbalance 130 are allowed to come to thermal equilibrium at a controlled temperature (29±0.5° C.). The data from the temperature sensor are automatically logged into the computer. A typical test may require 8 h for completion. In various embodiments, depending upon the configuration of the test cell 140 and other conditions, for example the volatile liquid or porous material, the test may require more or less than 8 h for completion.

Before each test, the membrane sample was wetted by immersing it in the testing liquid for at least 4 hours. The fully wetted membrane sample is then placed on the lower plate of the test cell. The upper part of the test cell was then placed over the lower plate and secured with six hexagonal nuts using a torque wrench at a pressure of 38 kPa to ensure that the same pressure was applied over the whole membrane sample surface.

Initially, the evaporation rate of IPA from the test cell was measured in order to quantify any mass error due to test cell leakage. In this experimental embodiment, it was determined that the test cell had a negligible leakage rate of $3.1 \times 10^{-9}$ mols$^{-1}$ C. Data Analysis In order to obtain pore-size distribution data, the mass data and experimental conditions are entered into an algorithm and the time at which pore-draining begins is determined. The software, which may be contained within a computer system having a processor unit and a memory, automatically calculates pore diameter and plots the cumulative mass within each bin (range of diameters grouped together). From these data the pore-size distribution based on the mass data is determined directly. If the pores are assumed to be right circular cylinders, one can obtain pore-size distribution based on the number of pores. Pore-size distribution based on mass or number of pores is then analyzed using a commercial statistical program to obtain the mean pore diameter and standard deviation of the pore-size distribution as follows.

An exemplary algorithm for analyzing the EP data was developed using Microsoft Office Excel 2003. The software requires the temperature, atmospheric pressure, test cell dimensions, and liquid properties as input parameters. In addition, the time at which the evaporation of the free-standing liquid is complete and pore-draining begins is also required and is determined from plots of the evaporation rate as a function of time. Primary data in the form of instantaneous mass as a function of time are tabulated on the spreadsheet. The mass data are then smoothed by determining the average mass for a 1-minute time interval; this is a "running average" whereby the average mass is determined at each consecutive point in time. The evaporation rate is determined by forward-differencing between consecutive average mass values.

Figure 4:
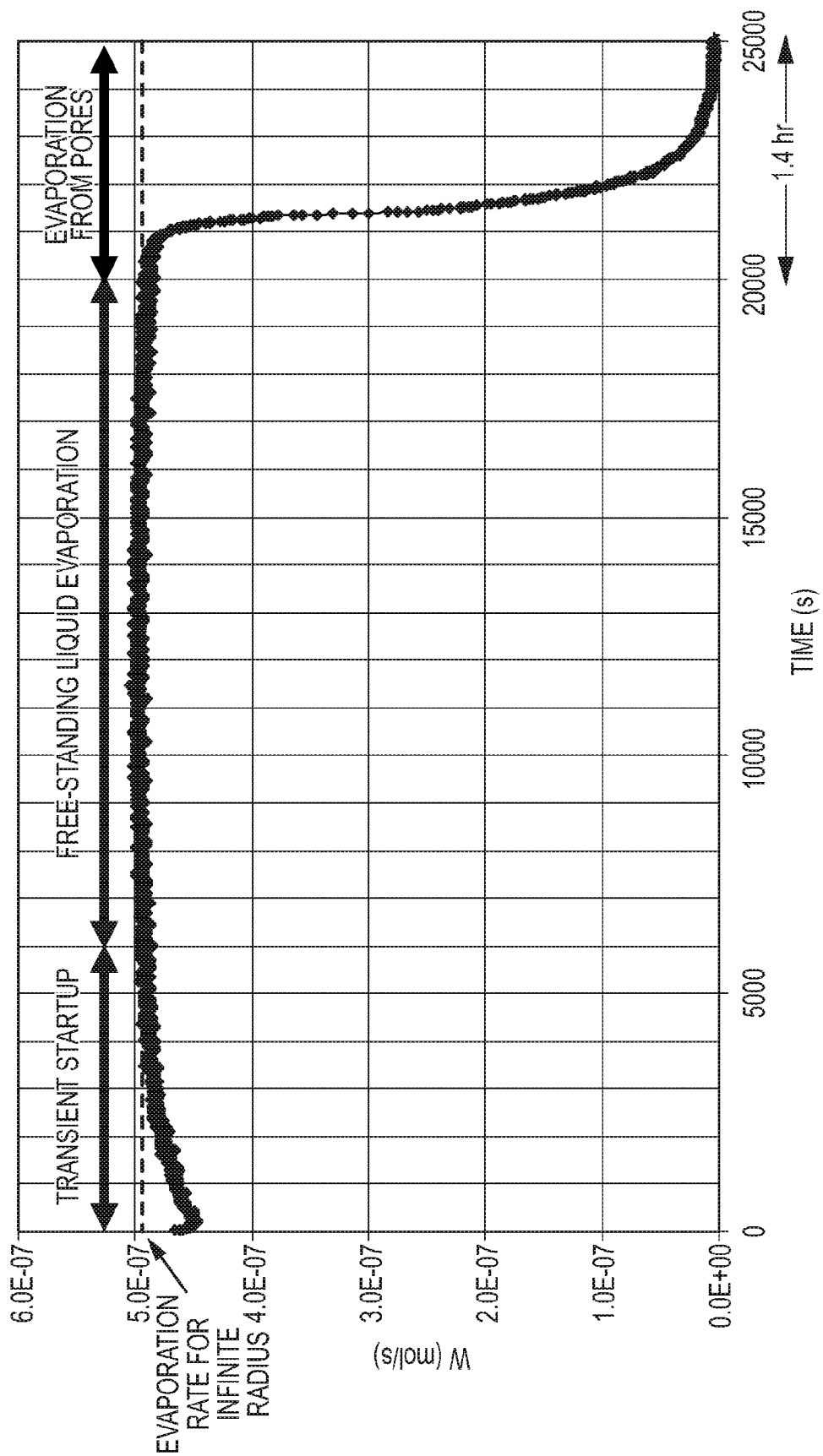
FIG. 4 is a representative graphical plot of evaporation rate (mol·s$^{-1}$) as a function of time (s); the results are used to obtain values of the experimentally determined input parameters required for determination of the pore-size distribution from a membrane sample.

Typical data for the mass-loss rate (W), in mols per second, as a function of time for evapoporometry characterization are shown in FIG. 4. Experimental data may be comprised of three periods: (1) transient, (2) surface-liquid evaporation, and (3) pore-liquid evaporation. During the transient period (~100 min under usual test conditions), the microbalance, test cell, and the evaporating volatile testing liquid are approaching the desired steady-state temperature. During this transient period, quasi-steady-state diffusion is also being established in the test cell.

After attaining steady-state temperature and quasi-steady-state diffusion, the surface-liquid evaporation period commences during which the mass is a linear function of time such that a constant mass-loss rate is obtained that corresponds to evaporation from the free-standing layer of volatile liquid. From the zero slope portion of the plot, the evaporation rate of the free-standing liquid ($W_0$) is determined via extrapolation to the y-axis.

Once this free-standing liquid layer has evaporated, the pore-liquid evaporation begins during which the mass versus time curve is concave upward corresponding to a monotonically decreasing mass-loss rate associated with evaporation from pores having progressively smaller diameters. The onset time for pore-liquid evaporation was determined via a regression analysis as the point of first departure from the freestanding liquid portion of the plot. The determination of complete evaporation of liquid from the pores was based on repeatability of the microbalance such that the mass difference between two subsequent values is less than 60 μg.

The evapoporometry characterization uses the mass versus time data during surface-liquid evaporation to determine the vapor pressure associated with a planar interface between the free-standing layer of volatile liquid and the ambient gas phase, i.e., $p_A^o$ in equation (2). It then uses the mass versus time data during pore-liquid evaporation to determine the vapor pressure associated with the curved interface between the volatile liquid within the pores that are draining at that instant of time and the ambient gas phase, i.e., $\bar{p}_A$ in equation (3). From these values of $p_A^o$ and $\bar{p}_A$, the instantaneous pore diameter can be determined from equation (1). The liquid mass within each physically significant pore is determined by forward differencing between adjacent pore diameters in time. Results are plotted as the cumulative mass within each bin (i.e., pore-size range) as a function of the average pore size of the bin.

Figure 5:
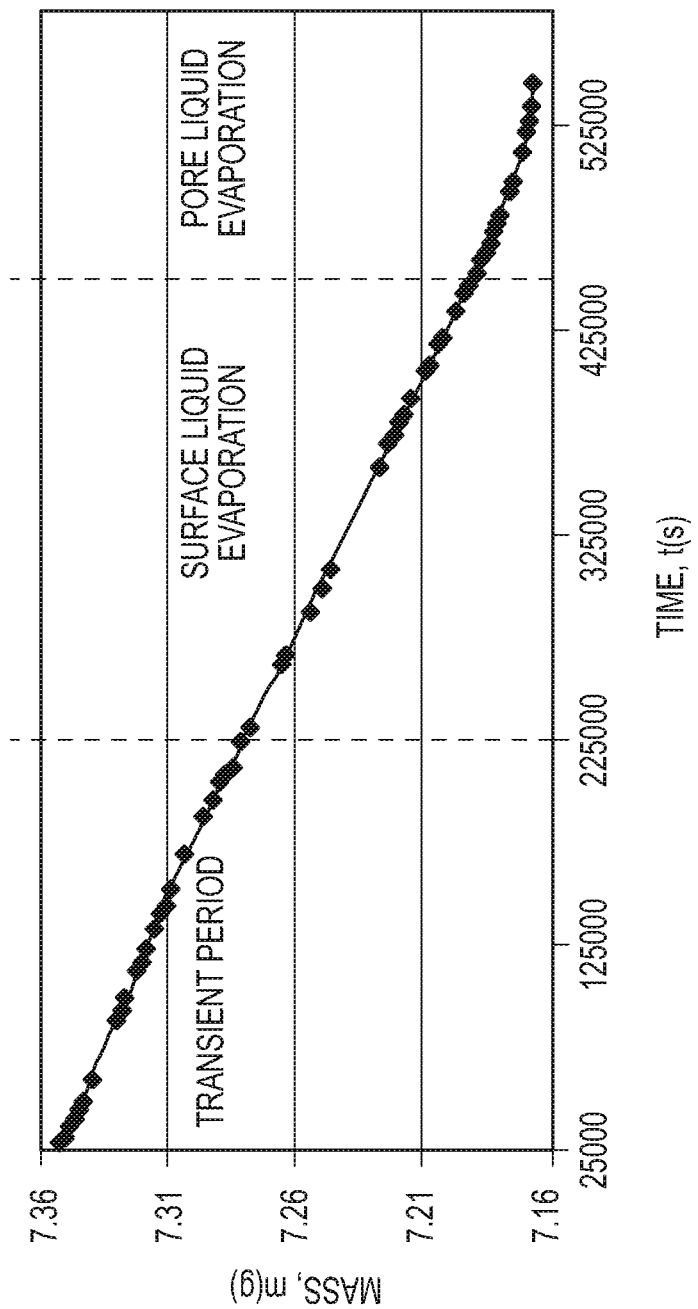
FIG. 5 is a representative graphical plot of typical mass (g) versus time (s) data for evaporation of a volatile liquid from the test cell used in evapoporometry characterization.

Typical data for the mass as a function of time for evapoporometry characterization are shown in FIG. 5. During the Transient Period, the microbalance, test cell, and the evaporating volatile liquid are coming to the steady-state temperature determined by the environmental chamber. During this Transient Period, quasi-steady-state diffusion is also being established in the test cell. After the steady-state temperature and quasi-steady-state diffusion have been established, the Surface-Liquid Evaporation period commences during which the mass is a linear function of time, thereby implying a constant mass-loss rate, corresponding to evaporation from the free-standing layer of volatile liquid. Once this free-standing liquid layer has evaporated, the Pore-Liquid Evaporation period commences during which the line describing the mass as a function of time is concave upward corresponding to a monotonically decreasing mass-loss rate associated with evaporation from pores having progressively smaller diameters. The evapoporometry characterization uses the mass versus time data during the Surface-Liquid Evaporation period to determine the vapor pressure associated with a planar interface between the free standing layer of volatile liquid and the ambient gas phase, i.e., $p_A^o$ in equation (1). It then uses the mass versus time data during the Pore-Liquid Evaporation period in order to determine the vapor pressure associated with the curved interface between the volatile liquid within the pores that are draining at that instant of time and the ambient gas phase, i.e., $\bar{p}_A$ in equation (1). From these values of $p_A^o$ and $\bar{p}_A$, the instantaneous pore diameter can be determined from equation (1).

Mass data obtained as explained above can be converted to number data assuming that the pores have a circular cross-section. Pore-size data based on mass and the number of pores were then transferred from the spreadsheet to Minitab commercial statistical software (e.g., Minitab Inc., State College, Pa.) for calculation and plotting the pore-size distribution. Pore-size distributions obtained via EP or SEM image analysis were fit with normal distributions, and mean and standard deviation of the distributions were calculated. Mean pore diameters and corresponding standard deviations of multiple membrane samples (replicates) were also calculated.

Figure 6:
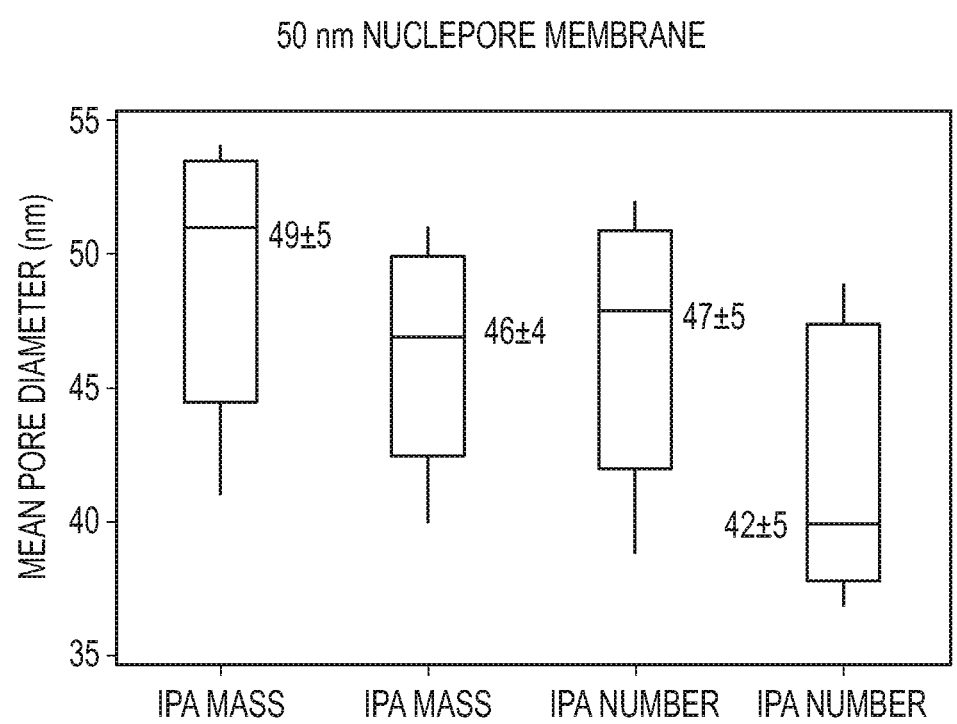
FIG. 6 is a graph showing evapoporometry results from a nominal 50 nm membrane using either isopropanol (IPA) and n-propanol (NPA) as the volatile liquid.

FIG. 6 shows mean pore-size diameters obtained using two different testing liquids (isopropanol (IPA) and n-propanol (NPA)). Results were compiled and presented in the form of box plots for the mass and pore number data. A horizontal line in the middle of each rectangular box represents the median observation of each distribution. The minimum and maximum values are located at the endpoint of the vertical line extended through the box. The top of the box represents the $75^{th}$ percentile, and the bottom of the box corresponds to the $25^{th}$ percentile; the larger the box, the greater the spread of the data. These points represent potential outliers. A paired samples t-test for means at significance level, $\alpha=0.05$, was used to determine statistical difference when membrane samples were tested with two different testing liquids. Analysis indicated no statistically significant difference between the mean pore diameter (n=5) using IPA and NPA. In various embodiments, other volatile liquids that do not interact with the porous membrane may be used. For example water, cyclohexane, butanol, ethanol, methanol, propanol, carbon tetrachloride, and non-interacting volatile liquids may be used.

Figure 7:
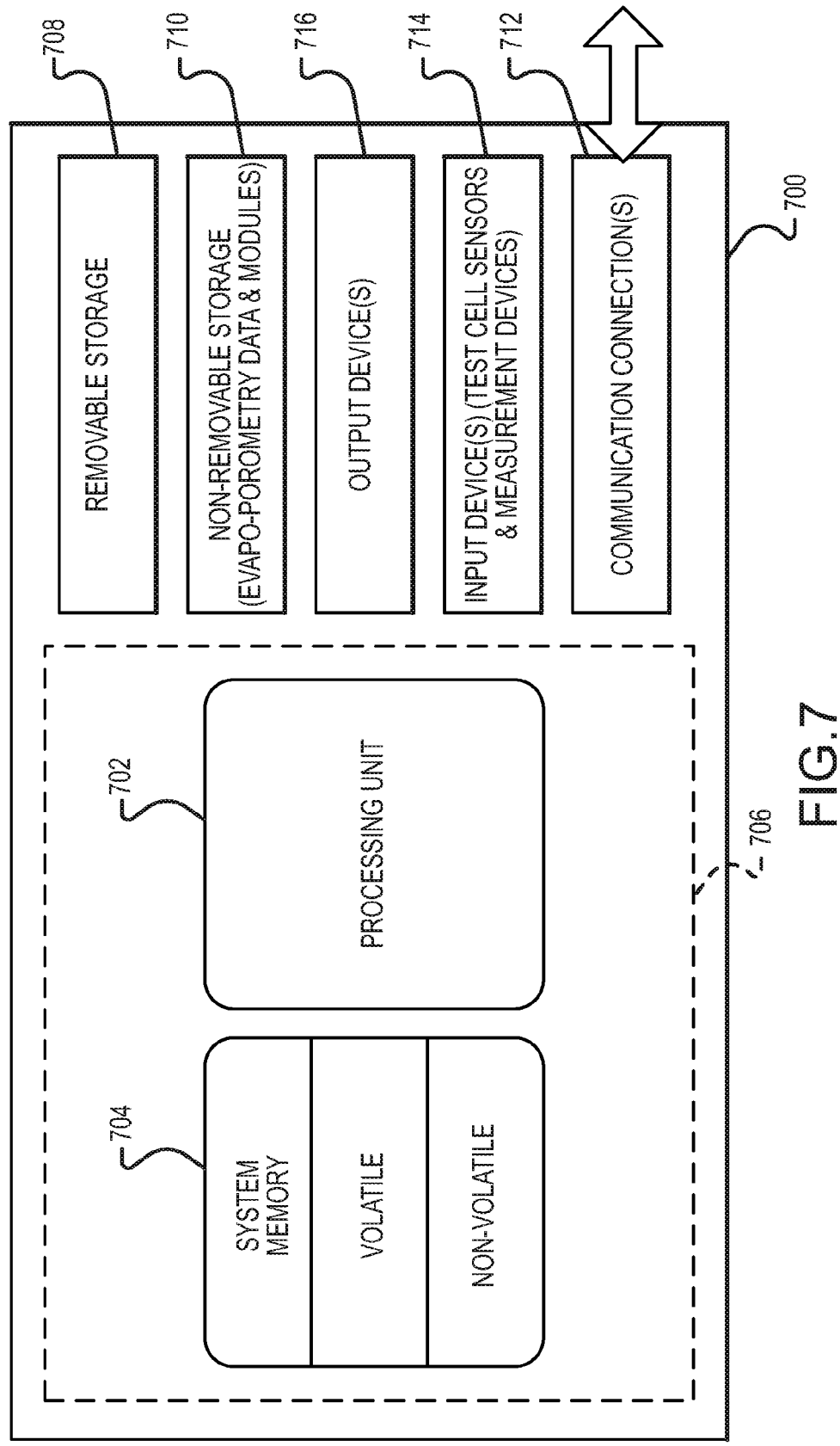
FIG. 7 is a schematic diagram of a computer system used for implementation of a software process used to perform pore size and pore-size distribution calculations for porous membrane samples.

FIG. 7 illustrates an exemplary computer system 700 configured by the software implementing the evapoporometry algorithms as described herein. In one implementation, the computer system 700 typically includes at least one processing unit 702 and memory 704. Depending upon the exact configuration and type of the computer system 700, the memory 704 may be volatile (e.g., RAM), non-volatile (e.g., ROM and flash memory), or some combination of both. The most basic configuration of the computer system 700 need include only the processing unit 702 and the memory 704 as indicated by the dashed line 706. In various embodiments the EP algorithms may be written to memory.

The computer system 700 may further include additional devices for memory storage or retrieval. These devices may be removable storage devices 708 or non-removable storage devices 710, for example, memory cards, magnetic disk drives, magnetic tape drives, and optical drives for memory storage and retrieval on magnetic and optical media. Storage media may include volatile and nonvolatile media, both removable and non-removable, and may be provided in any of a number of configurations, for example, RAM, ROM, EEPROM, flash memory, CD-ROM, DVD, or other optical storage medium, magnetic cassettes, magnetic tape, magnetic disk, or other magnetic storage device, or any other memory technology or medium that can be used to store data and can be accessed by the processing unit 702. Temperature readings, atmospheric pressure, vapor pressure, test cell dimensions, liquid properties, and other inputs may be stored on the storage device using any method or technology for storage of data, for example, computer readable instructions, data structures, and program modules. Software programs and files related thereto for processing the data collected from the test cell may be stored on the storage devices 708, 710 for processing by the processing unit 702.

The computer system 700 may also have one or more communication interfaces 712 that allow the system 700 to communicate with other devices. The communication interface 712 may be connected with a network. The network may be a local area network (LAN), a wide area network (WAN), a telephony network, a cable network, an optical network, the Internet, a direct wired connection, a wireless network, e.g., radio frequency, infrared, microwave, or acoustic, or other networks enabling the transfer of data between devices. Data are generally transmitted to and from the communication interface 712 over the network via a modulated data signal, e.g., a carrier wave or other transport medium. A modulated data signal is an electromagnetic signal with characteristics that can be set or changed in such a manner as to encode data within the signal.

The computer system 700 may further have a variety of input devices 714 and output devices 716. Exemplary input devices 714 may include a keyboard, a mouse, a tablet, a touch screen device, sensors, and measurement devices, for example a microbalance, temperature sensor, humidity sensor. Exemplary output devices 716 may include a display, a printer, and speakers. Such input devices 714 and output devices 716 may be integrated with the computer system 700 or they may be connected to the computer system 700 via wires or wirelessly, e.g., via IEEE 802.11 or Bluetooth protocol. These integrated or peripheral input and output devices are generally well known and are not further discussed herein. Other functions, for example, handling network communication transactions, may be performed by an operating system in the nonvolatile memory 704 of the computer system 700.

The technology described herein may be implemented as logical operations and/or modules in one or more systems. The logical operations may be implemented as a sequence of processor-implemented steps executing in one or more computer systems 700 and as interconnected machine or circuit modules within one or more computer systems. Likewise, the descriptions of various component modules may be provided in terms of operations executed or effected by the modules. The resulting implementation is a matter of choice, dependent on the performance requirements of the underlying system implementing the described technology. Accordingly, the logical operations making up the embodiments of the technology described herein are referred to variously as operations, steps, objects, or modules. Furthermore, it should be understood that logical operations may be performed in any order, unless explicitly claimed otherwise or a specific order is inherently necessitated by the claim language.

In some implementations, articles of manufacture are provided as computer program products that cause the instantiation of operations on a computer system to implement the invention. One implementation of a computer program product provides a computer program storage medium readable by a computer system and encoding a computer program. It should further be understood that the described technology may be employed in special purpose devices independent of a personal computer.

Evapoporometry offers several advantages over the current methods for determining pore size and pore-size distribution. No prior technique is capable of determining pore sizes over the full range of interest, which is typically from approximately the nanometer scale up to the micrometer scale. Techniques such as displacement porometry require relatively expensive dedicated equipment that involves the application of high pressures that can deform the material being studied. Moreover, displacement porometry can characterize only relatively large pores typically greater than 0.01 μm. Techniques such as gas adsorption/desorption also requires relatively expensive dedicated equipment that involves measuring the gas pressure very accurately. Moreover, gas adsorption/desorption relies on a phenomenon known as capillary condensation whereby pores fill by progressive adsorption. For this reason gas adsorption/desorption can accurately characterize only relatively small pores typically less than 0.01 μm. In addition, several techniques use hazardous materials, high temperatures, or high pressures in characterizing porosity. These may tend to alter or destroy the porous material, limiting both reproducibility of the techniques and their applicability to various materials.

Techniques such as scanning electron microscopy (SEM) require a very expensive instrument that can measure the pore size only within a planar surface that may have a sample area as small as only a few hundred square micrometers. As such, SEM does not characterize the pore size throughout a porous sample of interest but rather provides a two-dimensional measure of a three-dimensional characteristic whereby the pore size may not be representative. Image analysis of SEM scans becomes a challenge when pores are not cylindrical. Other less commonly used pore-size characterization techniques such as thermo-porometry and perm-porometry also require dedicated relatively expensive equipment and are difficult to implement reliably.

In contrast to other techniques, evapoporometry uses a conventional microbalance to measure the mass loss as a function of time from the porous material that is contained with an appropriately designed test cell. Moreover, evapoporometry permits characterizing pore size from a few nanometers up to near micrometer scale, a range of particular practical interest. Since it is a non-destructive technique, evapoporometry can provide accurate pore-size distribution characteristics before and after the porous material is subject to a process that could change the distribution characteristics, for example the imposition of a mechanical stress (e.g., compaction), heat, or fouling.

For these reasons, evapoporometry offers a relatively simple, inexpensive, and reproducible technique for characterizing the pore-size and distribution of a variety of porous materials. The following are various examples which demonstrate the wide applicability and robustness of evapoporometry. The following examples were generated using a test cell of constant diameter and wherein the boundary conditions were as described in equations (1) through (12).

EXAMPLES

Example 1

Track-Etched Polycarbonate Membranes

FIGS. 8A-10C show the pore-size distribution determined by evapoporometry for nominal 10, 50 and 100 nm track-etched polycarbonate (Nuclepore™) membranes. Pore-size data is plotted as percent total mass as a function of pore diameter. The resulting mass-based distribution can be converted to a number-based distribution by assuming cylindrical pores. The mass-based ($d_m$) and number-based ($d_n$) are shown as solid and dashed vertical lines, respectively. FESEM or SEM was also used to determine distribution data and the number-based pore diameter.

Figure 8A:
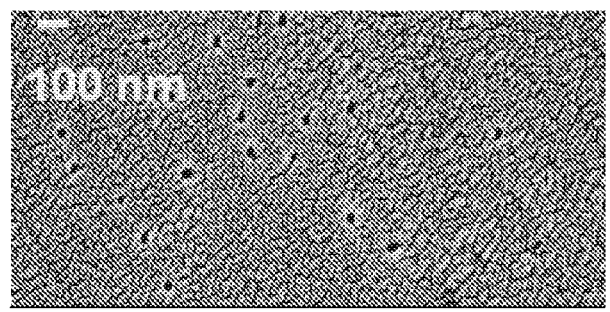
FIG. 8A is a FESEM micrograph of a nominal 10 nm Nuclepore™ membrane.
Figure 8B:
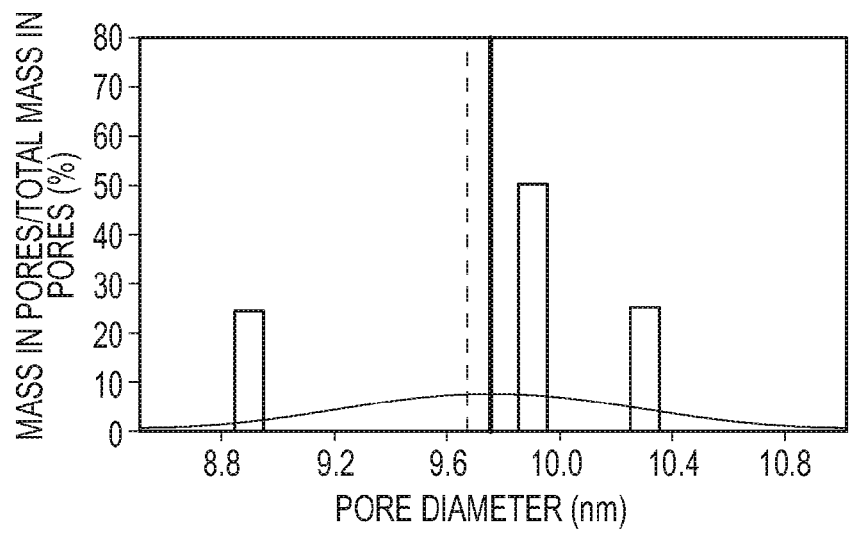
FIG. 8B is a pore-size distribution graph for a 10 nm Nuclepore™ membrane determined by evapoporometry, where the solid and dashed lines show the mass-based ($d_m$) and number-based ($d_n$) mean pore diameter, respectively.
Figure 8C:
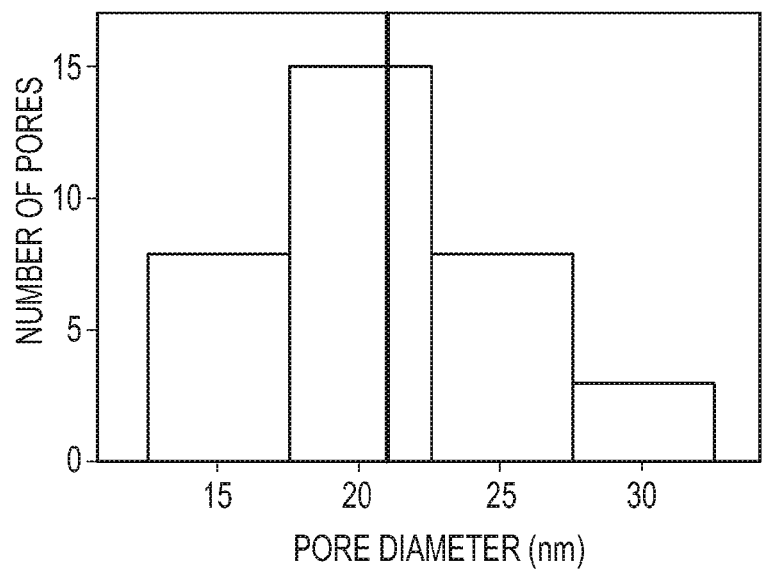
FIG. 8C is a pore-size distribution graph for the 10 nm membrane shown in FIG. 8A determined by FESEM image analysis.

FIG. 8A is a FESEM micrograph of a sample section of nominal 10 nm Nuclepore™, track-etched polycarbonate membrane. The normal distribution for this membrane determined by EP is shown in FIG. 8B. Based on the graph in FIG. 8B, the $d_m$ and $d_n$ were calculated to be 9.8±0.5 nm and 9.7±0.5 nm, respectively. The average $d_m$ and $d_n$ for two replicate runs were 11±1 nm and 10±0 nm, respectively. FESEM characterization, shown in FIG. 8C, gave a $d_n$ of 21±4 nm (the average over all samples tested was 20±0 nm). FESEM characterization by Kim and Stephens (J. Membr. Sci. 123, 303 (1997)) gave 14±2 nm and atomic force microscopy (AFM) characterization by Dietz et al. (J. Membr. Sci. 65, 101 (1992)) gave 18 nm.

Figure 9A:
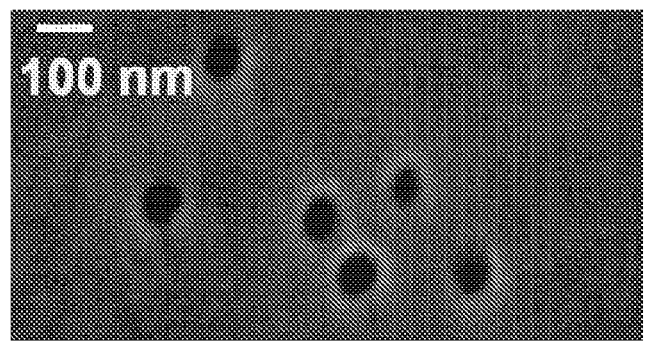
FIG. 9A is a SEM micrograph of a nominal 50 nm Nuclepore™ membrane.
Figure 9B:
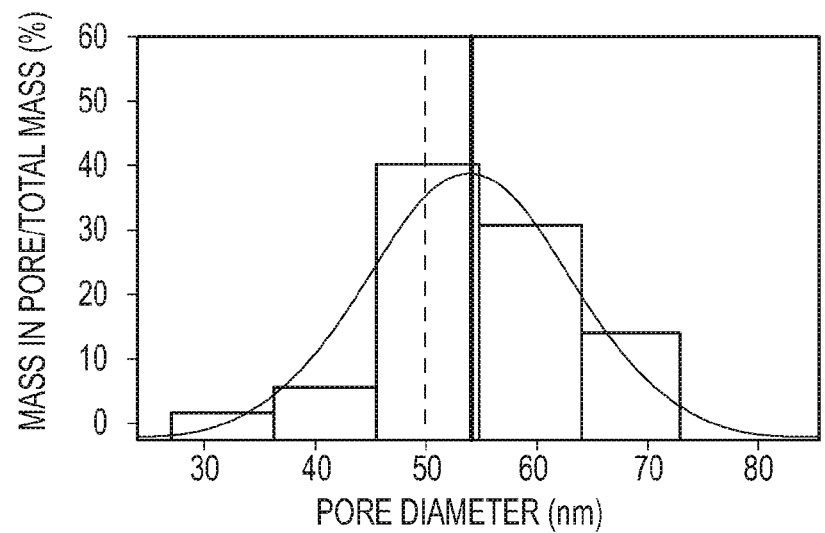
FIG. 9B is a pore-size distribution graph for a 50 nm Nuclepore™ membrane determined by evapoporometry, where the solid and dashed lines show the mass-based ($d_m$) and number-based ($d_n$) mean pore diameter, respectively.
Figure 9C:
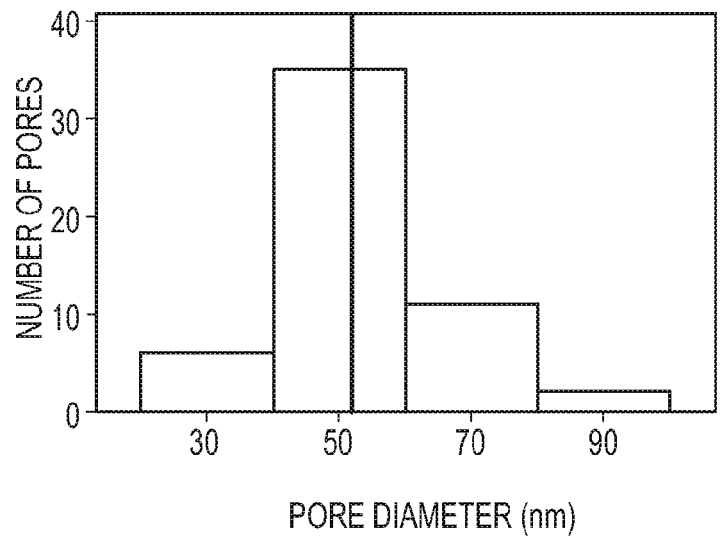
FIG. 9C is a pore-size distribution graph for the 50 nm membrane shown in FIG. 9A determined by SEM image analysis.

FIG. 9A is a SEM micrograph of a section of nominal 50 nm Nuclepore™ track-etched polycarbonate membrane. The normal distribution for this membrane, determined by EP, is shown in FIG. 9B. Based on the graph in FIG. 9B, the $d_m$ and $d_n$ were determined to be 54±10 nm and 50±11 nm, respectively. The $d_m$ and $d_n$ for five replicate runs were 49±5 nm and 47±5 nm. SEM characterization, shown in FIG. 9C, gave a $d_n$ of 52±12 nm (the average over all samples tested was 53±2 nm). FESEM characterization by Kim and Stephens (J. Membr. Sci. 123, 303 (1997)) gave 39±1 nm and the AFM characterization by Dietz et al. (J. Membr. Sci. 65, 101 (1992)) gave 66 nm.

Figure 10A:
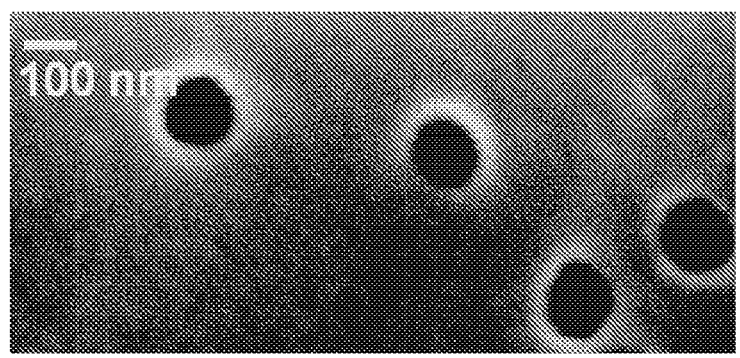
FIG. 10A is a SEM micrograph of a nominal 100 nm Nuclepore™ membrane.
Figure 10B:
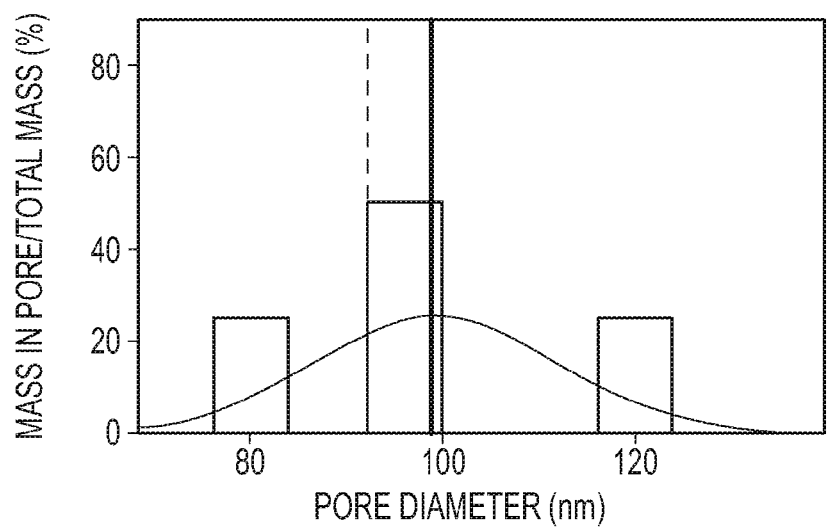
FIG. 10B is a pore-size distribution graph for a 100 nm Nuclepore™ membrane determined by evapoporometry, where the solid and dashed lines show the mass-based ($d_m$) and number-based ($d_n$) mean pore diameter, respectively.
Figure 10C:
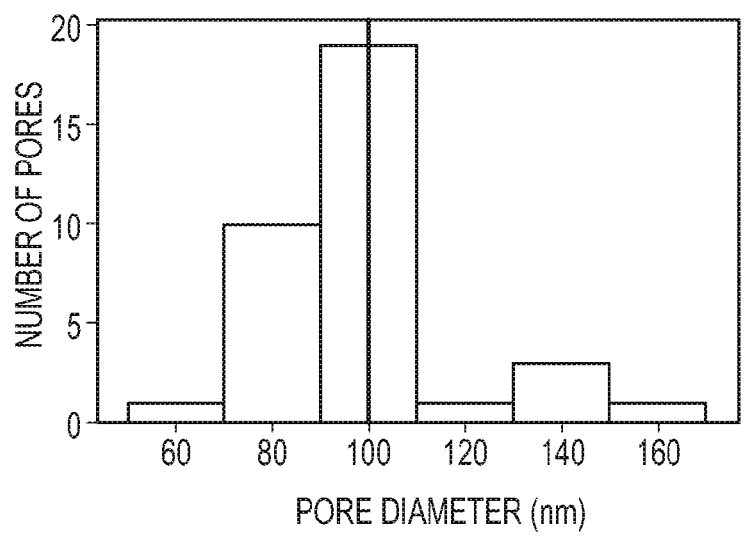
FIG. 10O is a pore-size distribution graph for the 100 nm membrane shown in FIG. 10A determined by SEM image analysis.

FIG. 10A is a SEM micrograph of a section of nominal 100 nm Nuclepore™ track-etched polycarbonate membrane. The normal distribution for this membrane, determined by EP, is shown in FIG. 10B. Based on the distribution shown in FIG. 10B, the $d_m$ and $d_n$ were determined to be 99±13 nm and 96±12 nm, respectively. The average $d_m$ and $d_n$ for five replicate runs were 82±12 nm and 79±13 nm. SEM characterization, shown in FIG. 10C, gave a $d_n$ of 100±20 nm (the average over all samples tested was 106±10 nm). FESEM characterization by Kim and Stephens (J. Membr. Sci. 123, 303 (1997)) gave 74±4 nm, AFM characterization by Dietz et al. (J. Membr. Sci. 65, 101 (1992)) gave 113 nm, and SEM characterization by Villa-Martinez et al. (J. Membr. Sci. 65, 19 (1988)) gave 87±19 nm.

The pore diameter values determined by evapoporometry compare well with the nominal pore diameters of these track-etched polycarbonate (Nuclepore™) membrane standards. The EP-determined values also compare well with FESEM and SEM characterization as well as published SEM, FESEM and AFM. The accuracy of evapoporometry is indicated by the small error for replicate runs on different membrane samples. Re-measurement of the same membrane sample gave similar reproducibility.

Example 2

Aluminum Oxide Membranes

FIGS. 11A-12C show pore-size distribution determined by evapoporometry for nominal 20 nm and 100 nm aluminum oxide (Anopore™) membranes. The evapoporometry data in these figures is plotted as the percent of the total mass as a function of pore diameter. The resulting mass-based distribution can be converted to a number-based distribution by assuming cylindrical pores. The mass-based ($d_m$) and number-based ($d_n$) are shown as solid and dashed vertical lines, respectively. FESEM or SEM was also used to determine distribution data and the number-based pore diameter.

Figure 11A:
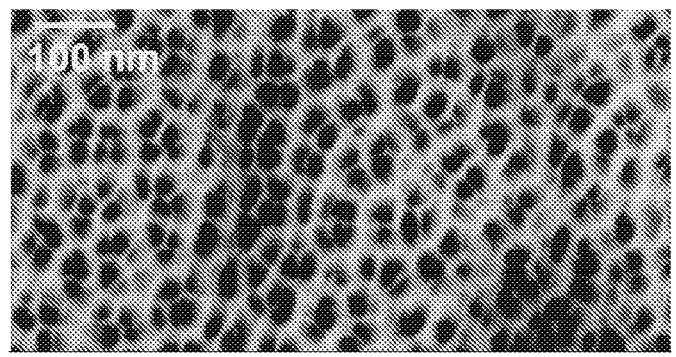
FIG. 11A is a FESEM micrograph of a nominal 20 nm Anopore™ membrane.
Figure 11B:
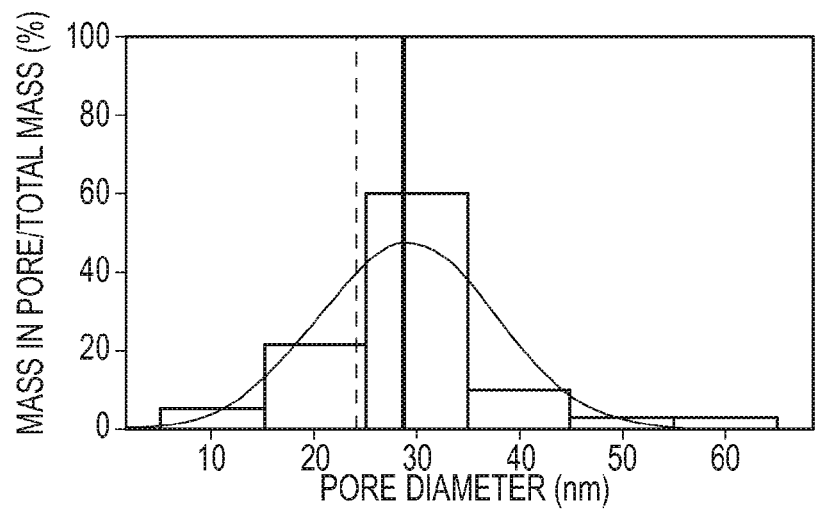
FIG. 11B is a pore-size distribution graph for a 20 nm Anopore™ membrane determined by evapoporometry, where the solid and dashed lines show the mass-based ($d_m$) and number-based ($d_n$) mean pore diameter, respectively.
Figure 11C:
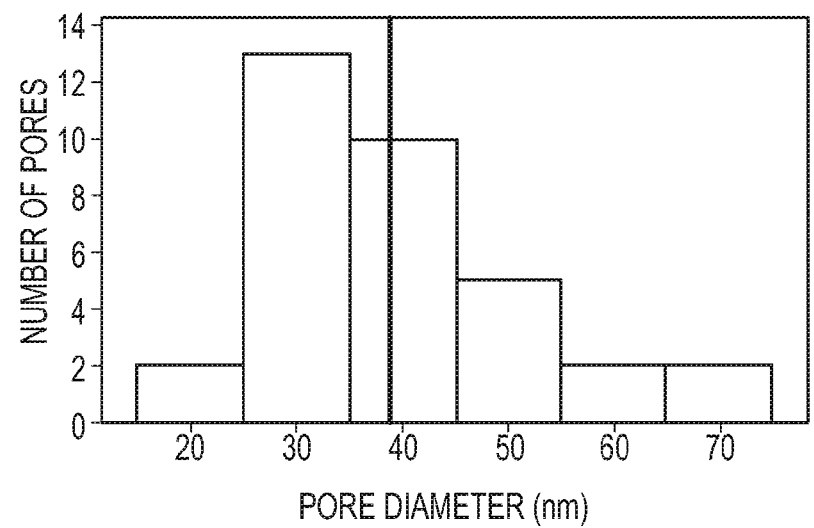
FIG. 11C is a pore-size distribution graph for the 20 nm Anopore™ membrane shown in FIG. 11A determined by FESEM image analysis.

FIG. 11A is a micrograph of a section of nominal 20 nm Anopore™ aluminum oxide membrane. The normal distribution for this membrane, determined by EP, is shown in FIG. 11B. Based on the distribution shown in FIG. 11B, the $d_m$ and $d_n$ were determined to be 29±9 nm and 24±8 nm, respectively. FESEM characterization, shown in FIG. 11C, gave a $d_n$ of 39±11 nm (the average over all samples was 37±6 nm), AFM characterization by Bowen et al. (J. Membr. Sci. 110, 233 (1996)) gave 28±8 nm.

Figure 12A:
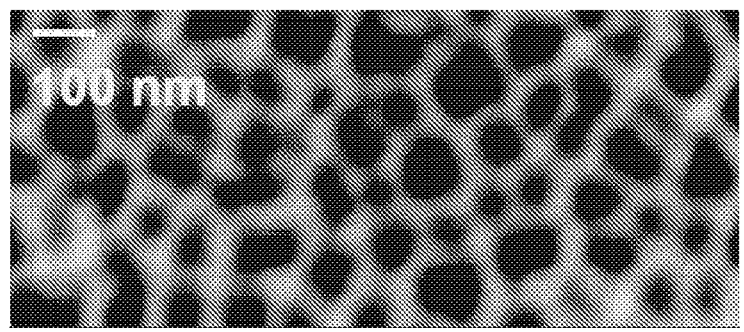
FIG. 12A is a SEM micrograph of a nominal 100 nm Anopore™ membrane.
Figure 12B:
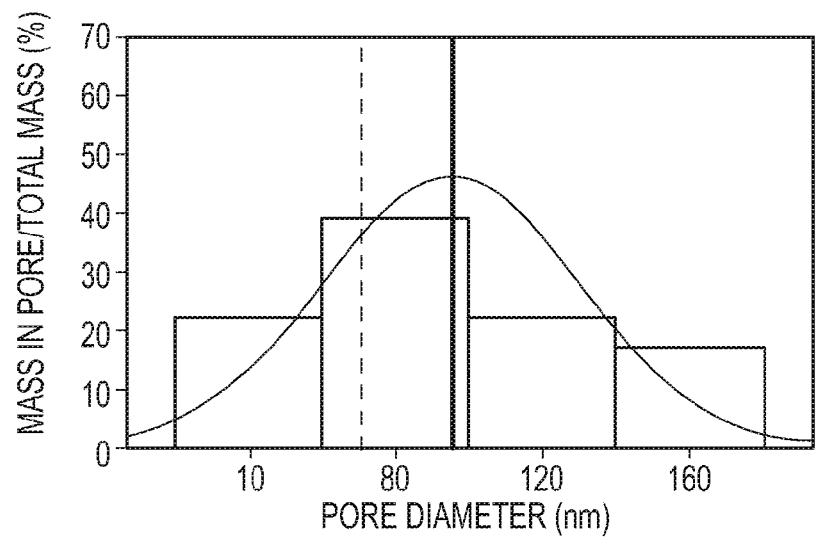
FIG. 12B is a pore-size distribution graph for a 100 nm Anopore™ membrane determined by evapoporometry, where the solid and dashed lines show the mass-based ($d_m$) and number-based ($d_n$) mean pore diameter, respectively.
Figure 12C:
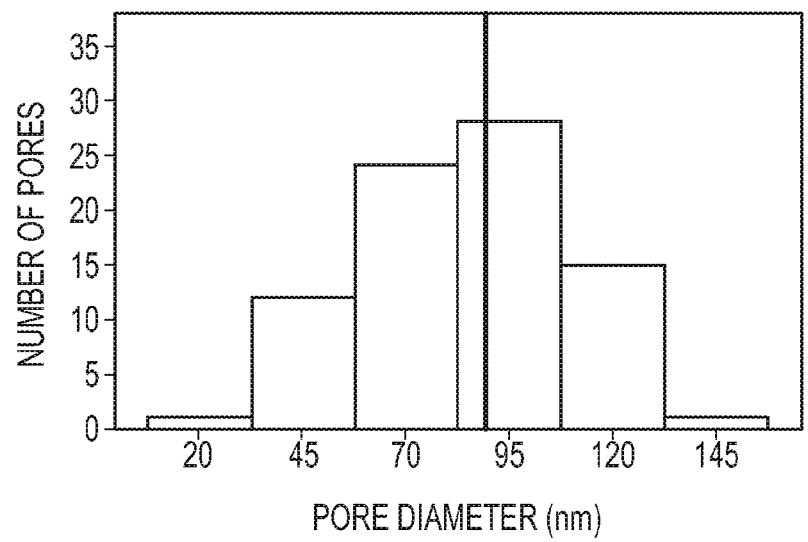
FIG. 12C is a pore-size distribution graph for the 100 nm Anopore™ membrane shown in FIG. 12A determined by SEM image analysis.

FIG. 12A is a SEM micrograph of a section of nominal 100 nm Anopore™ aluminum oxide membrane. The normal distribution for this membrane, determined by EP, is shown in FIG. 12B. Based on the distribution shown in FIG. 12B, the $d_m$ and $d_n$ were determined to be 95±35 nm and 70±28 nm, respectively. The average $d_m$ and $d_n$ for five replicate runs were 97±13 nm and 80±15 nm. SEM characterization, shown in FIG. 12C, gave a $d_n$ of 86±26 nm (the average over all samples tested was 86±10 nm). SEM characterization by Hernandez et al. (J. Membr. Sci. 137, 89 (1997)) gave 83±25 nm and AFM characterization by Bowen et al. (J. Membr. Sci. 110, 233 (1996)) gave 108±26 nm.

The pore diameter values determined by evapoporometry compare well with the nominal pore diameters of these aluminum oxide (Anopore™) membrane standards. The EP-determined values compare well with FESEM and SEM characterization as well as published SEM, FESEM and AFM. The accuracy of evapoporometry is indicated by the small error for replicate runs on different membrane samples. Re-measurement of the same membrane sample gave similar reproducibility.

Example 3

Pressure on Poly(Vinylidene Fluoride) (PVDF) Membranes

It was of interest to compare evapoporometry with liquid displacement porometry (LDP) for a commercial ultrafiltration (UF) membrane containing a broad distribution of irregular interconnected pores. Evapoporometry was used to characterize the pore-size distribution of nominal 20 nm (FIG. 13) and 50 nm (FIG. 14) commercial PVDF membranes. In these figures EP results are plotted as percent total mass as a function of pore diameter. The mass-based ($d_m$) and number-based ($d_n$) are shown as solid and dashed vertical lines, respectively.

Figure 13A:
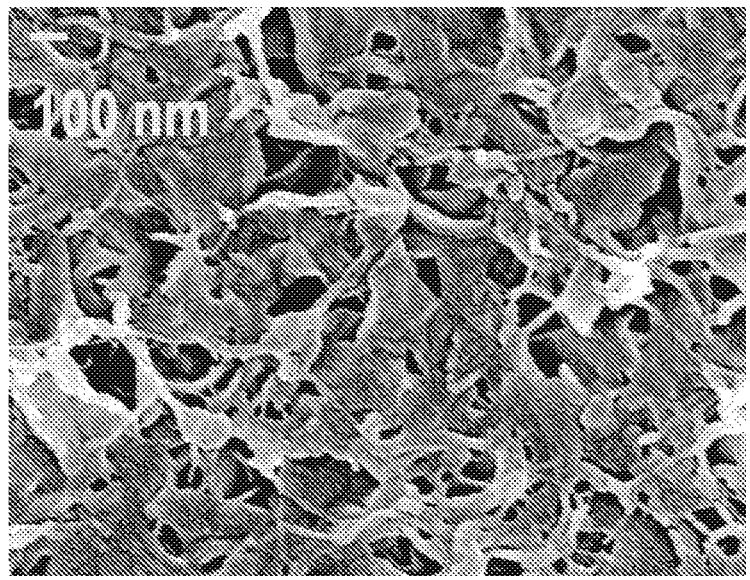
FIG. 13A is a FESEM micrograph of a nominal 20 nm poly(vinylidene fluoride) (PVDF) membrane.
Figure 13B:
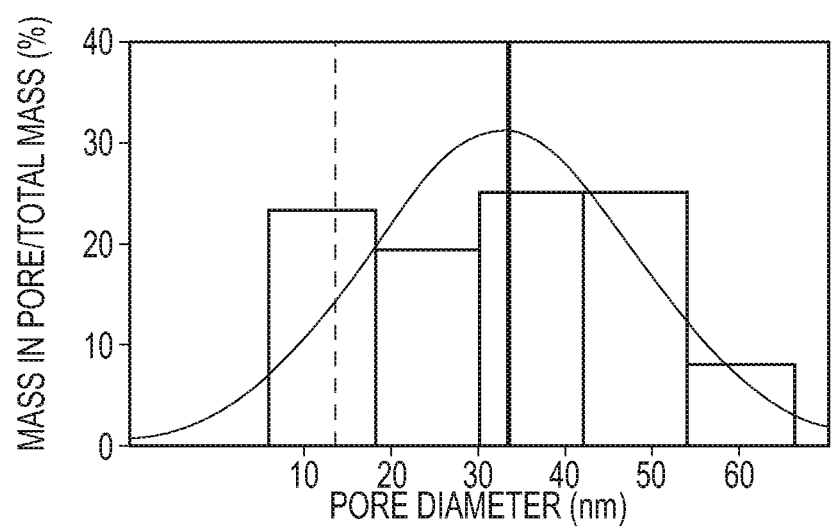
FIG. 13B is a pore-size distribution graph expressed as percent mass as a function of pore diameter determined by evapoporometry on a nominal 20 nm PVDF membrane, where the solid and dashed lines show the mass-based ($d_m$) and number-based ($d_n$) mean pore diameter, respectively.

FIG. 13A is a FESEM micrograph of a section of nominal 20 nm PVDF membrane. FIG. 13B is a graph of the normal distribution of this membrane determined by EP. The $d_m$ and $d_n$, from the graph in FIG. 13B, were determined to be 33±15 nm and 14±11 nm, respectively. The average $d_m$ and $d_n$ for three replicate runs were 37±5 nm and 18±5 nm. LDP characterization (X. Yang of Nanyang Technological University) gave a $d_n$ of 24±3 nm.

Figure 14A:
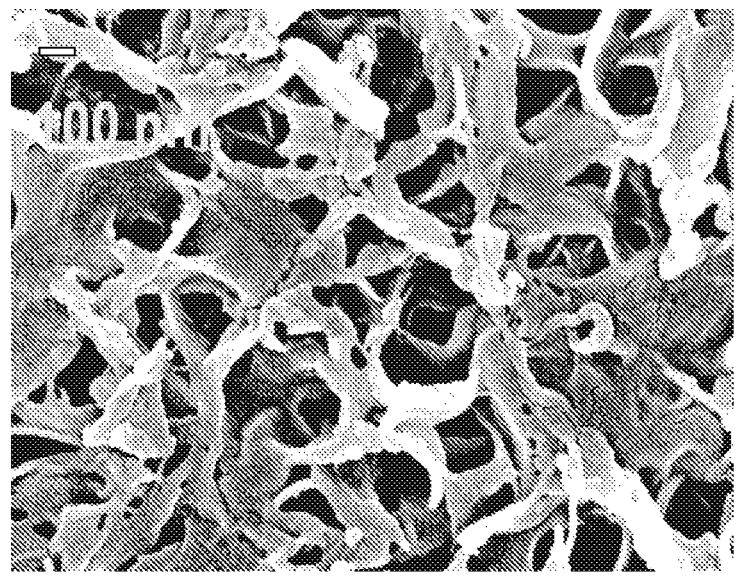
FIG. 14A is a FESEM micrograph of a nominal 50 nm PVDF membrane.
Figure 14B:
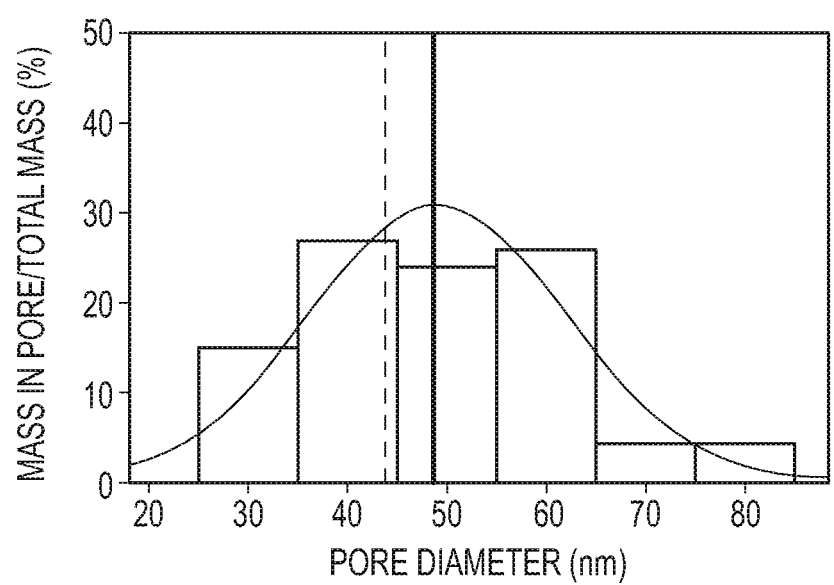
FIG. 14B is a pore-size distribution graph expressed as percent mass as a function of pore diameter determined by evapoporometry on a nominal 50 nm PVDF membrane, where the solid and dashed lines show the mass-based ($d_m$) and number-based ($d_n$) mean pore diameter, respectively.

FIG. 14A is a FESEM micrograph of a section of nominal 50 nm PVDF membrane. The $d_m$ and $d_n$ based on the normal distribution shown in FIG. 14B were determined to be 49±13 nm and 43±11 nm, respectively. The average $d_m$ and $d_n$ for three replicate runs were 47±9 nm and 40±11 nm. LDP (X. Yang of Nanyang Technological University) gave a $d_n$ of 43±5 nm.

Example 4

Pressure

Figure 15A:
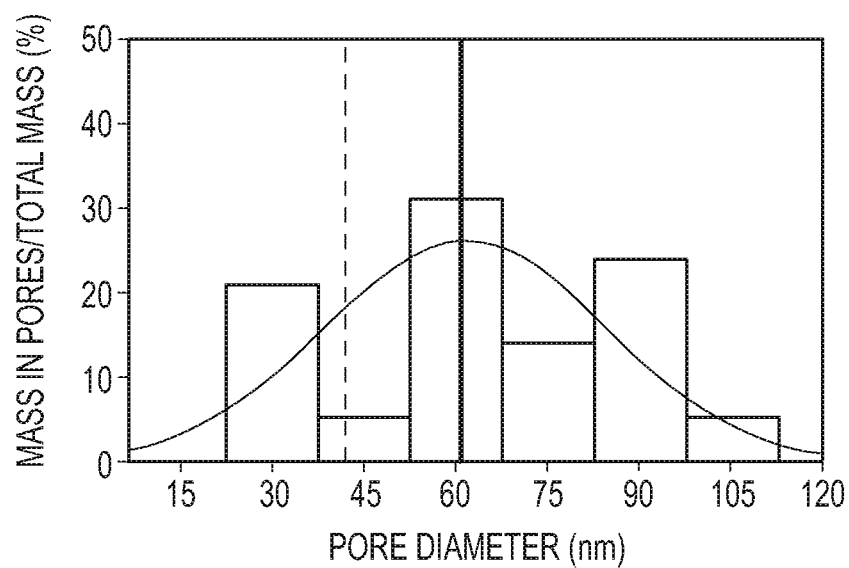
FIG. 15A is a graph showing evapoporometry determination of the pore-size distribution of a nominal 50 nm PVDF membrane for zero pressure differential applied, where the solid and dashed lines show the mass-based ($d_m$) and number-based ($d_n$) mean pore diameter, respectively.
Figure 15B:
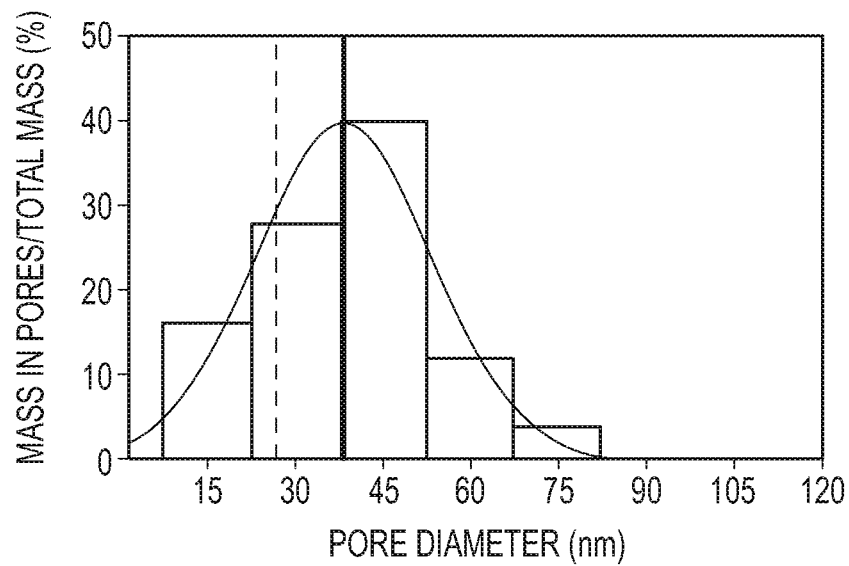
FIG. 15B is a graph showing evapoporometry determination of the pore-size distribution of a nominal 50 nm PVDF membrane for 0.1 MPa pressure differential applied for one hour, where the solid and dashed lines show the mass-based ($d_m$) and number-based ($d_n$) mean pore diameter, respectively.

Applying high pressures to porous materials, such as in LDP, could change the membrane morphology. In order to assess the effect of applying sustained high pressure to these polymeric membranes, evapoporometry was used to characterize the pore-size distribution before and after subjecting the same membrane to a pressure of 0.1 MPa for one hour. FIGS. 15A and 15B show the pore-size distribution determined by evapoporometry expressed as percent mass as a function of pore diameter for a nominal 50 nm commercial PVDF membrane. FIG. 15A shows the $d_m$ and $d_n$ based on the normal distribution is 62±23 nm and 42±20 nm, respectively. FIG. 15B shows the pore-size distribution after the same membrane was subjected to a 0.1 MPa pressure differential for one hour. The pore-size distribution is shifted markedly toward smaller pores. The $d_m$ and $d_n$ based on the normal distribution shown in FIG. 15B is 38±15 nm and 27±12 nm, respectively. The fact that the LDP gave slightly smaller $d_n$ values than evapoporometry for the data shown in FIGS. 14A and 14B may be the consequence of not using the same membrane sample for the two characterization techniques. FIGS. 15A and 15B clearly establish that evapoporometry provides a more reliable method than LDP for characterizing small pores.

Example 5

Hollow Fibers

Figure 16A:
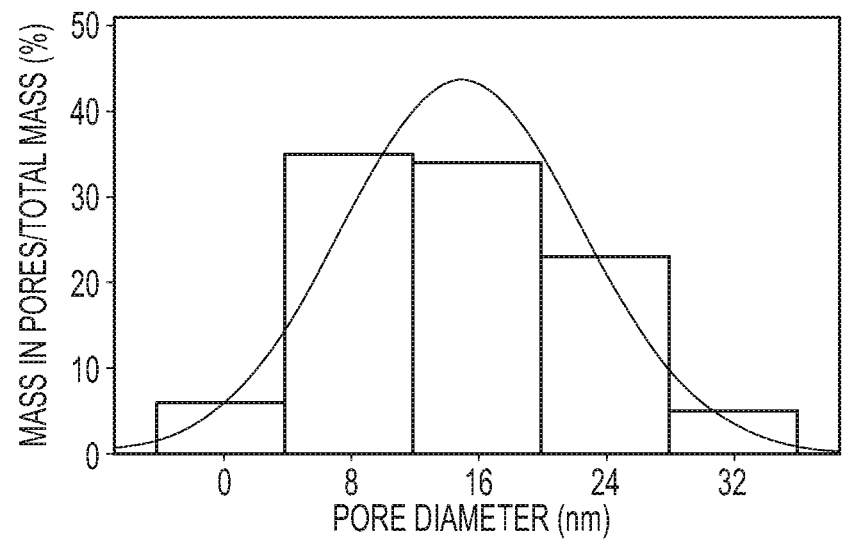
FIG. 16A shows a pore-size determination graph obtained from a porous hollow fiber membrane material, where the pore-size distribution was determined by evapoporometry.
Figure 16B:
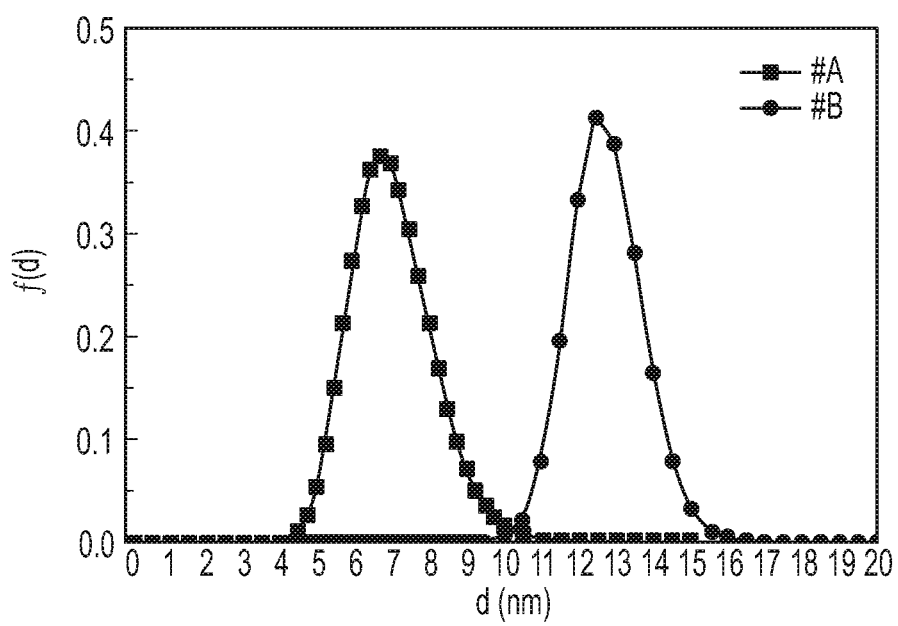
FIG. 16B shows a pore-size determination graph obtained from a porous hollow fiber membrane material, where the pore-size distribution was determined by size exclusion. The size-exclusion result corresponds to the hollow fiber membrane sample labeled #B.

A representative EP result for a hollow fiber membrane is presented in FIG. 16A (on left with square data points). The polyethersulfone hollow fiber membranes used in this study were fabricated and obtained from Nanyang Technological University (NTU), Singapore. These hollow fibers have an outer diameter of ~1300 μm and an inner diameter of ~1000 μm, and were characterized by NTU via size exclusion (SE) using a 2000 ppm dextrane aqueous solution. SE results, shown in FIG. 16B (on right with circle data points), indicated that the hollow fibers have a narrow pore-size distribution with pore diameter of 12.7±1.08 nm (geometric standard deviation) Wang et al. (J. Memb. Sci. (2010) 355: 158-167).

A total of two EP tests were conducted such that each test used a different set of randomly selected hollow fibers. Results from the tests indicate mass-based pore-size distribution results of 14±6 nm and 15±8 nm, and size-based pore-size distribution results of 11±5 nm and 13±5 nm, respectively, for the two tests. The mass-based results indicating a pore-size distribution of 15±8 nm is shown in FIG. 16A. These EP results compare quite favorably with results obtained via size exclusion indicating a pore-size distribution of 12.7±1.08 nm (geometric standard deviation) by Wang et al. (J. Memb. Sci. (2010) 355: 158-167).

Example 6

Internal Fouling

PVDF membrane samples with 50 nm and 100 nm nominal pore sizes were fouled with polystyrene microspheres (e.g., Polysciences, Inc., Warrington, Pa.). Samples of the 50-nm PVDF membranes were prepared by cutting 47-mm diameter coupons from a single membrane roll. These coupons were then fouled with 50 nm microspheres (Polybead® Microspheres) in a dead-end flow cell configuration filtering 10-mL aqueous solution containing $3.5 \times 10^{-7}$ per mL of 50 nm microspheres using a laboratory vacuum pressure system. Samples of the 100-nm PVDF membranes were prepared by cutting 20×12 cm coupons from a single membrane roll. These coupons were then fouled in a cross-flow flat-sheet cell with an aqueous feed solution that contained $3 \times 10^{-9}$ per mL of 100 nm microspheres (Polybead® Microspheres) at a feedside pressure of 0.07 MPa (10 psi). The manufacturer reported the sizes of the two samples of microspheres were 50 and 100 nm, respectively, with a coefficient of variance of 15%.

In order to acquire an accurate image of a membrane structure containing microspheres, an embedding technique used in biological applications involving wet samples was adapted. Membrane samples are exposed in graded ethanol series: 30%, 50%, 70%, 95%, and 100% (three times each) for 30 min so that water is systematically replaced with ethanol. Then, the membrane samples are transitioned into Epon-Araldite (Eponate 12™-Araldite 502 Kit, Ted Pella, Inc, Redding, Calif.) resin in ratios in this order: (1) 2:1 acetone:Epon for 1-3 hours; (2) 1:1 acetone:Epon for 1-3 hours; (3) 1:2 acetone:Epon for 1-3 hours; (4) full strength Epon without accelerator for 1-3 hours; and (5) full-strength Epon with accelerator for 1 hour. The embedded membrane samples were then placed between two treated microscope slides and then polymerized at 60° C. overnight. Slides treated with a polytetrafluoroethylene (PTFE) release agent separated easily after polymerization leaving a thin wafer of sample embedded in resin. Sections of sample were then excised using a scalpel and remounted on an appropriate stub for cross-sectional viewing via Field Emission Scanning Electron Microscope (FESEM, Model JSM-7401F, JOEL Ltd, Japan).

Figure 17A:
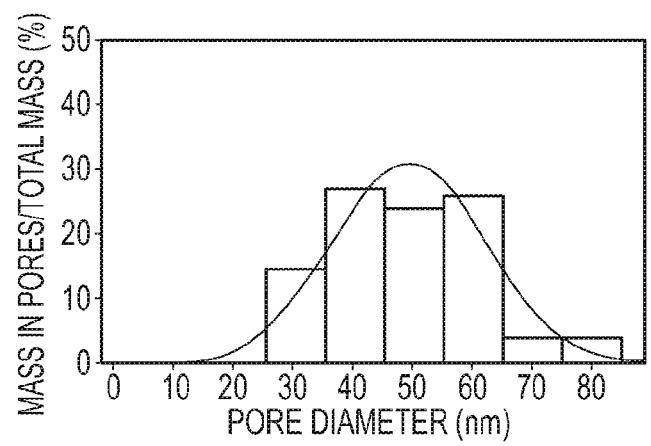
FIG. 17A shows the pore-size distribution of a nominal 50 nm PVDF membrane determined by evapoporometry before fouling with 50 nm microspheres.
Figure 17B:
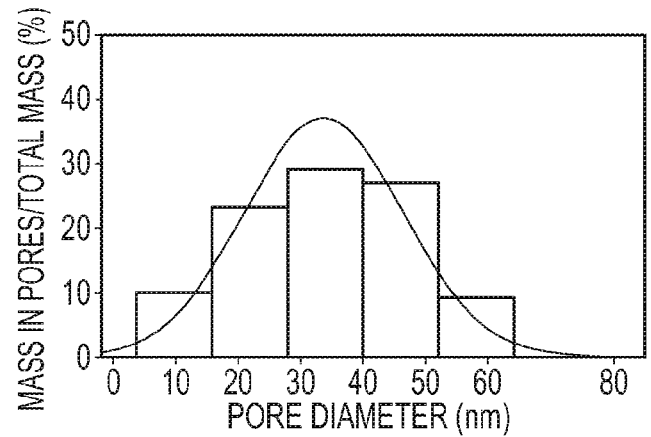
FIG. 17B shows the pore-size distribution of a nominal 50 nm PVDF membrane determined by evapoporometry after fouling with 50 nm microspheres.
Figure 17C:
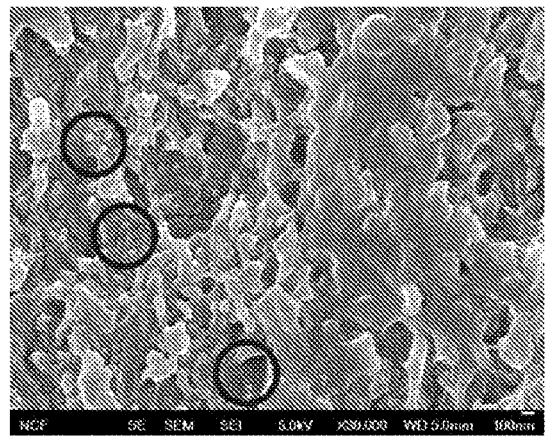
FIG. 17C is a FESEM micrograph of a 50 nm PVDF membrane fouled with 50 nm microspheres.

Representative pore-size distribution results obtained via EP (based on mass data) for a virgin 50-nm PVDF are presented in FIG. 17A. The EP results are expressed in terms of percent mass as a function of pore diameter (units: nm). EP results indicate that this membrane has an overall mean pore diameter of 47±9 nm (standard deviation of three replicated samples). In FIG. 17B (right) a pore-size distribution (based on mass data) obtained via EP for an internally fouled 50-nm PVDF membrane is presented. The results indicate that when fouled with 50 nm microspheres, the mean pore size decreases to 33±1 nm (standard deviation of three replicated samples). An FESEM micrograph of the cross section of the embedded 50-nm PVDF membrane clearly shows the presence of the 50 nm microspheres in the membrane pores. In FIG. 17C, the microspheres are visible within dark circles in the micrograph.

Figure 18A:
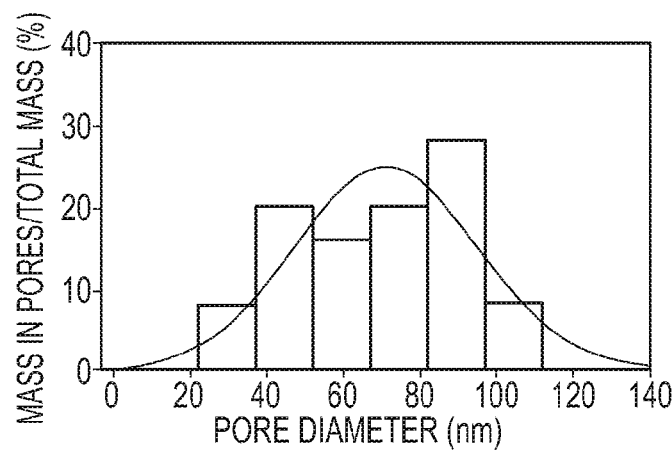
FIG. 18A shows the pore-size distribution of a nominal 100 nm PVDF membrane determined by evapoporometry before fouling with 100 nm microspheres.
Figure 18B:
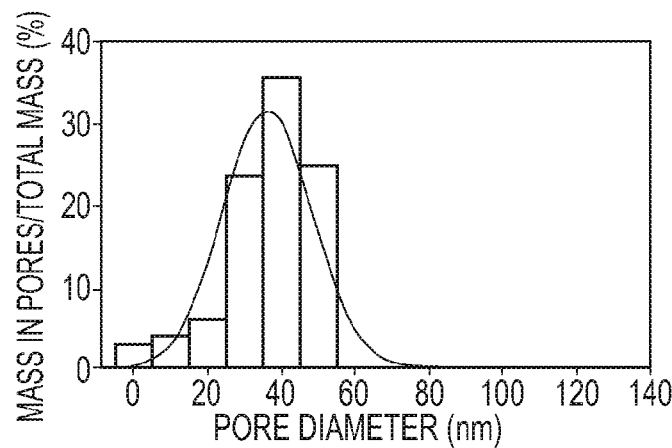
FIG. 18B shows the pore-size distribution of a nominal 100 nm PVDF membrane determined by evapoporometry after fouling with 100 nm microspheres.
Figure 18C:
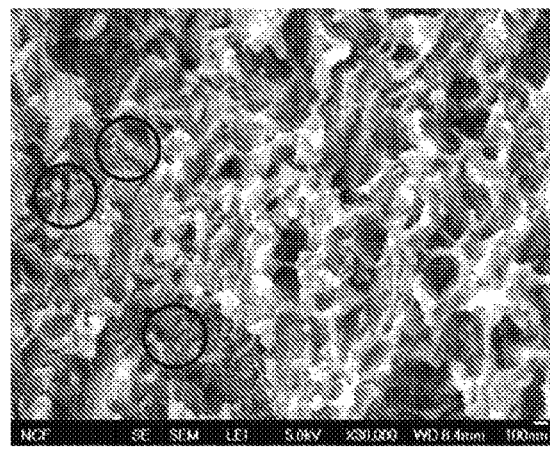
FIG. 18C is a FESEM micrograph of a 100 nm PVDF membrane fouled with 100 nm microspheres.

EP tests for a virgin 100-nm PVDF membrane indicate that this membrane has an overall mean pore diameter of 78±14 nm (standard deviation of three replicated samples) based on the mass data as shown in FIG. 18A. A representative EP result for an internally fouled 100-nm PVDF membrane is presented in FIG. 18B. The results indicate that when fouled with 100 nm microspheres, the overall mean pore diameter decreases to 52±14 nm (standard deviation of three replicated samples) based on the mass data. An FESEM micrograph of the cross-section of the embedded 100-nm PVDF membrane clearly shows the presence of the 100 nm microspheres in the membrane pores. In FIG. 18C, the microspheres are visible within dark circles in the micrograph.

All directional references (e.g., proximal, distal, upper, lower, upward, downward, left, right, lateral, longitudinal, front, back, top, bottom, above, below, vertical, horizontal, radial, axial, clockwise, and counterclockwise) are only used for identification purposes to aid the reader's understanding of the present invention, and do not create limitations, particularly as to the position, orientation, or use of the invention. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. The exemplary drawings are for purposes of illustration only and the dimensions, positions, order and relative sizes reflected in the drawings attached hereto may vary.

The above specification, examples and data provide a complete description of the structure and use of exemplary embodiments of the invention. Although various embodiments of the invention have been described above with a certain degree of particularity, or with reference to one or more individual embodiments, those skilled in the art could make numerous alterations to the disclosed embodiments without departing from the spirit or scope of this invention. Other embodiments are therefore contemplated. It is intended that all matter contained in the above description and shown in the accompanying drawings shall be interpreted as illustrative only of particular embodiments and not limiting. Changes in detail or structure may be made without departing from the basic elements of the invention as defined in the following claims.

What is claimed is:

1. An apparatus for determining pore size in a porous membrane material comprising
    a microbalance;
    a test cell for receiving the porous membrane material placed upon the microbalance, wherein
        the test cell is formed as a diffusion chamber with a top open to atmosphere and a base;

the test cell is configured to hold the porous membrane material as a sole covering to an opening in the base and the test cell has a seal structure positioned around a perimeter of the opening in the base and outside a perimeter edge of the porous membrane material and configured to prevent lateral liquid and vapor loss between the porous membrane material and the base of the test cell;

a temperature sensor configured to measure a temperature within the test cell; and a computing device connected to receive data output from both the microbalance of mass measurements over a period of time and the temperature sensor over the period of time and configured to calculate a pore size of pores in the porous membrane material based upon the data output.

2. The apparatus of claim 1, wherein the seal structure is configured to contact the porous membrane material.

3. The apparatus of claim 1 wherein the test cell further comprises a base plate and an upper portion, the upper portion comprising an upper opening defining the top and a lower opening, the lower opening positioned proximal to the base plate; and the seal structure is positioned between the base plate and the upper portion and is configured to seal against the porous membrane material.

4. The apparatus of claim 3, wherein the upper portion of the test cell is formed as a circular cylinder with an open upper end positioned distal to the base plate.

5. The apparatus of claim 3, wherein the base plate comprises a recess for accepting the porous membrane material.

6. The apparatus of claim 3, wherein a cross-sectional area of the lower opening is greater than or equal to a cross-sectional area of the upper opening.

7. The apparatus of claim 3, wherein the upper portion of the test cell defines a length between the upper and lower openings that is equal to or greater than 10 times the diameter of the lower opening.

8. The apparatus of claim 3, wherein the base plate is configured to receive the porous membrane material directly upon an upper surface thereof such that an entire surface area of the porous membrane material is fully supported by the base plate.

9. The apparatus of claim 1 further comprising an environmental chamber in which the test cell is positioned in order to maintain an isothermal temperature within the test cell.

10. The apparatus of claim 9 further comprising a temperature sensor positioned within the environmental chamber to monitor temperature and provide feedback to the environmental chamber for maintaining the isothermal temperature.

11. The apparatus of claim 1 further comprising a material, device, or mechanism positioned within the environmental chamber to mitigate static charge.

12. The apparatus of claim 11, wherein the static mitigating material, device, or mechanism is a polonium source.

13. The apparatus of claim 1 further comprising an anti-vibration platform upon which the microbalance is supported.

14. A method for determining pore size and pore-size distribution in a porous membrane material comprising:

placing a porous membrane material sample at a base of a test cell that forms a diffusion chamber open to atmosphere above the porous membrane material sample;

introducing a volume of a volatile liquid within the test cell on an upper surface of the porous membrane material sample;

placing the test cell on a microbalance;

maintaining the test cell and microbalance at a constant temperature;

measuring a mass of the test cell over a period of time to determine an evaporation rate;

relating the evaporation rate to a vapor pressure at an interface between the volatile liquid in the porous membrane material sample and an ambient gas phase within the test cell; and relating the vapor pressure to a pore diameter.

15. The method of claim 14 further comprising creating a vapor-tight seal between the base of the test cell, the upper portion of the test cell, and the porous membrane material sample.

16. The method of claim 14 further comprising saturating the porous membrane material sample with the volatile liquid before placing the porous membrane material sample at the bottom of the test cell.

17. The method of claim 14, wherein the volatile liquid is a wetting liquid.

18. The method of claim 14, wherein the volatile liquid is a non-wetting liquid.

19. The method of claim 14, wherein the volatile liquid is selected from isopropanol or n-propanol.

20. The method of claim 14 further comprising housing the test cell in an environmental chamber.

21. The method of claim 20 further comprising positioning a material, device, or mechanism within the environmental chamber to mitigate static charge.

22. The method of claim 14 further comprising supporting the test cell and the microbalance on an anti-vibration table.

23. The method of claim 14 further comprising determining a mass loss of the volatile liquid for each of a transient period, a surface-liquid evaporation period, and a pore-liquid evaporation period to determine the evaporation rate.

24. The method of claim 14, wherein the porous membrane material is one or more hollow fibers.

25. A method for determining pore-size distribution in a porous membrane material comprising determining a pore diameter by placing a porous membrane material sample at a base of a test cell to form a diffusion chamber open to atmosphere;

introducing a volume of a volatile liquid within the test cell on an upper surface of the porous membrane material sample;

placing the test cell on a microbalance;

maintaining the test cell at constant temperature;

measuring a mass of the test cell over a period of time to determine an evaporation rate;

relating the evaporation rate to a vapor pressure at an interface between the volatile liquid in the porous membrane material sample and an ambient gas phase within the test cell; and relating the vapor pressure to one or more pore diameters;

determining a cumulative mass loss of the volatile liquid for each of the one or more pore diameters; and calculating a number of pores of a particular pore size based upon a corresponding cumulative mass loss and by approximating a form of pores as circular.

26. The method of claim 25 further comprising determining the mass loss of the volatile liquid for each of a transient period, a surface-liquid evaporation period, and a pore-liquid evaporation period.

27. A method of determining pore size and pore-size distribution of a porous membrane material, the method comprising
   placing a porous membrane material in a test cell that forms a diffusion chamber above the porous membrane material open to atmosphere;
   saturating the porous membrane material with a volatile liquid;
   directly covering the porous membrane material with a volume of the volatile liquid sufficient to cover the porous membrane material;
   maintaining the test cell at constant temperature;
   measuring the mass of the test cell as a function of time
   recording time-dependent mass measurements and temperature values of the test cell and in a memory device; and
   calculating the pore size and pore-size distribution of pores in the porous membrane material based upon the time-dependent mass measurements and temperature values recorded in the memory device using a computing device connected to the memory device.

28. A method for use in characterizing pore size and pore-size distribution of a porous membrane material, the method comprising:
   placing a porous membrane material in a test cell that forms a diffusion chamber above the porous membrane material open to atmosphere, wherein the porous membrane material is saturated and overlaid with a volume of volatile liquid sufficient to cover the porous membrane material;
   collecting mass readings from a microbalance at a series of first time intervals;
   recording the mass and time;
   averaging mass readings data over a second series of time intervals;
   forward-differencing between consecutive average mass values to determine an evaporation rate; and
   converting the evaporation rate to pore size.

* * * * *